(12) United States Patent
Muramatsu et al.

(10) Patent No.: US 12,263,231 B2
(45) Date of Patent: Apr. 1, 2025

(54) ADENO-ASSOCIATED VIRUS VIRIONS FOR TREATMENT OF EPILEPSY

(71) Applicants: Jichi Medical University, Tochigi (JP); Gene Therapy Research Institution Co., Ltd., Kawasaki (JP)

(72) Inventors: Shin-ichi Muramatsu, Tochigi (JP); Keiji Oguro, Tochigi (JP); Kuniko Shimazaki, Tochigi (JP)

(73) Assignees: Jichi Medical University, Tochigi (JP); Gene Therapy Research Institution Co., Ltd., Kawasaki (JP)

( * ) Notice: Subject to any disclaimer, the term of this patent is extended or adjusted under 35 U.S.C. 154(b) by 114 days.

(21) Appl. No.: 17/732,901

(22) Filed: Apr. 29, 2022

(65) Prior Publication Data
US 2022/0275399 A1 Sep. 1, 2022

Related U.S. Application Data

(62) Division of application No. 16/069,370, filed as application No. PCT/JP2017/001048 on Jan. 13, 2017, now abandoned.

(51) Int. Cl.
| | |
|---|---|
| A61K 48/00 | (2006.01) |
| A61K 35/761 | (2015.01) |
| A61K 38/17 | (2006.01) |
| A61K 45/06 | (2006.01) |
| A61P 25/08 | (2006.01) |
| A61P 25/28 | (2006.01) |
| C07K 14/705 | (2006.01) |
| C12N 15/864 | (2006.01) |

(52) U.S. Cl.
CPC .......... *A61K 48/005* (2013.01); *A61K 35/761* (2013.01); *A61K 38/177* (2013.01); *A61K 45/06* (2013.01); *A61K 48/0075* (2013.01); *A61P 25/08* (2018.01); *A61P 25/28* (2018.01); *C07K 14/705* (2013.01); *C12N 15/8645* (2013.01); *A61K 48/0058* (2013.01); *C12N 2750/14122* (2013.01); *C12N 2750/14143* (2013.01)

(58) Field of Classification Search
CPC .................................................. A61K 48/005
See application file for complete search history.

(56) References Cited

U.S. PATENT DOCUMENTS

| | | | |
|---|---|---|---|
| 2009/0098631 A1 | 4/2009 | Fitzsimons et al. | |
| 2017/0028002 A1 | 2/2017 | Byrne et al. | |

FOREIGN PATENT DOCUMENTS

| | | | |
|---|---|---|---|
| WO | 03/093479 A1 | 11/2003 | |
| WO | 2008/016629 A2 | 2/2008 | |
| WO | 2008/124724 A1 | 10/2008 | |
| WO | 2010/037143 A1 | 4/2010 | |
| WO | 2012/057363 A1 | 5/2012 | |
| WO | 2014/160092 A1 | 10/2014 | |

OTHER PUBLICATIONS

Shaimardanova et al. Frontiers of Molecular Neuroscience. vol. 15, Article 868531. pp. 1-10, 2022 (Year: 2022).*
Cappella et al. International Journal of Molecular Science 20,4388: doi.org/10.3390/ijms20184388. pp. 1-21 (Year: 2019).*
Hitti et al. Parkinsonisn and Related Disorders. 2019. //dio.org/10. 1016/j.parkrekdis.2019.07.018. pp. 1-9 (Year: 2019).*
Kohl et al., "Hippocampal Neuroligin-2 Overexpression Leads to Reduced Aggression and Inhibited Novelty Reactivity in Rats," PLOS One, 8: e56871 (2013).
Noe et al., "Gene therapy of focal onset epilepsy using adeno-associated virus vector-mediated overexpression of neuropeptide," Jasper's Basic Mechanisms of the Epilepsies, 1-17 (2012).
Kullmann et al., "Gene therapy in epilepsy—is it time for clinical trials?" Nature Reviews Neurology, 10: 300-304 (2014).
Fang et al., Neuroligin-1 Knockdown Suppresses Seizure Activity by Regulating Neuronal Hyperexcitability, Molecular Neurobiology, 53: 270-284 (2016).
Oguro et al., "Gene therapy for epileptic EL mice by intravascular administration of Adeno-associated virus," Tenkan Kenkyu, 33: 521 O 2-89 (2015).
Raol et al., "Enhancing GABAA Receptor alpha1 Subunit Levels in Hippocampal Dentate Gyrus Inhibits Epilepsy Development in an Animal Model of Temporal Lobe Epilepsy," The Journal of Neuroscience, 26: 11342-11346 (2006).
Oguro et al., "Gene therapy for epileptic EL mice by intravascular administration of Adeno-associated virus," Tenkan Kenkyu, 34: 442, ES9-4 (2016).
Duque et al., "Intravenous Administration of Self-complementary AAV9 Enables Transgene Delivery to Adult Motor Neurons," Molecular Therapy, 17: 1187-1196 (2009).
Extended European Search Report issued in corresponding European Patent Application No. 17738541.6 dated Aug. 20, 2019.

(Continued)

*Primary Examiner* — Marcia S Noble
(74) *Attorney, Agent, or Firm* — Morgan, Lewis & Bockius LLP

(57) ABSTRACT

Provided is a novel gene therapy means for neurological diseases including epilepsy. The present invention provides: a recombinant adeno-associated virus vector for use in the treatment of neurological diseases including epilepsy, which comprises a polynucleotide encoding a protein capable of improving the excitation-inhibiting function of an inhibitory synapse in vivo, preferably neuroligin-2 protein; a pharmaceutical composition comprising said recombinant vector; and others. The present invention also provides a method for treating a disease such as epilepsy using the recombinant vector.

6 Claims, 6 Drawing Sheets
Specification includes a Sequence Listing.

(56) References Cited

International Search Report issued in corresponding International Patent Application No. PCT/JP2017/001048 dated Feb. 28, 2017.
NCBI AAV1 capsid protein list printed Nov. 6, 2020 (2020).
NCBI AAV2 capsid protein list printed Nov. 6, 2020 (2020).
NCBI AAV9 capsid protein list printed Nov. 6, 2020 (2020).

* cited by examiner

[Fig. 1]
a. NL2(+) FLAG antibody staining
b. NL2(-) FLAG antibody staining
[Fig. 2]
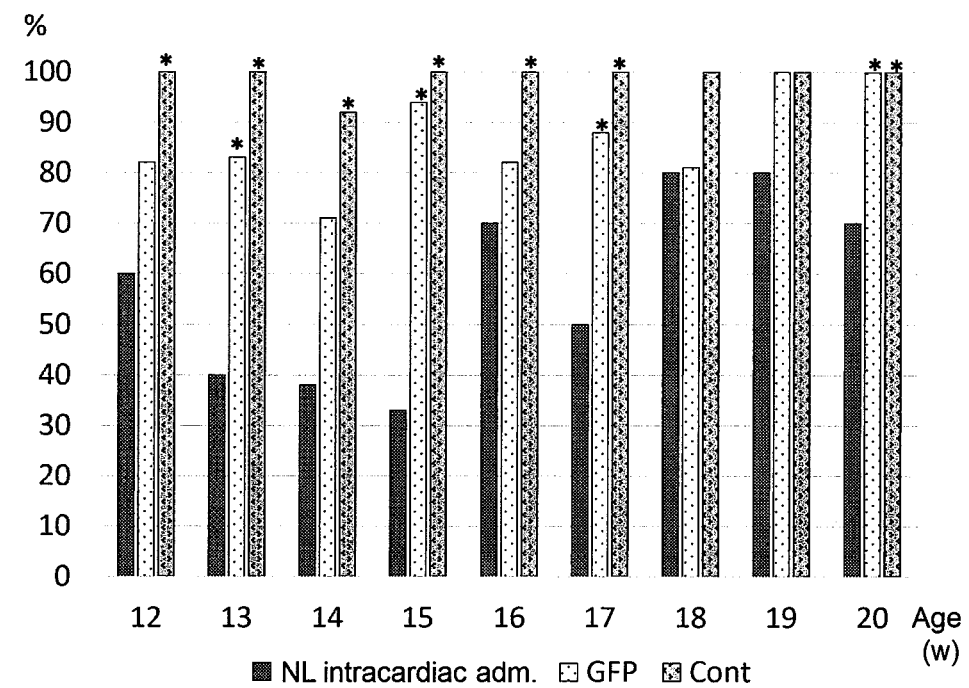

[Fig. 3]
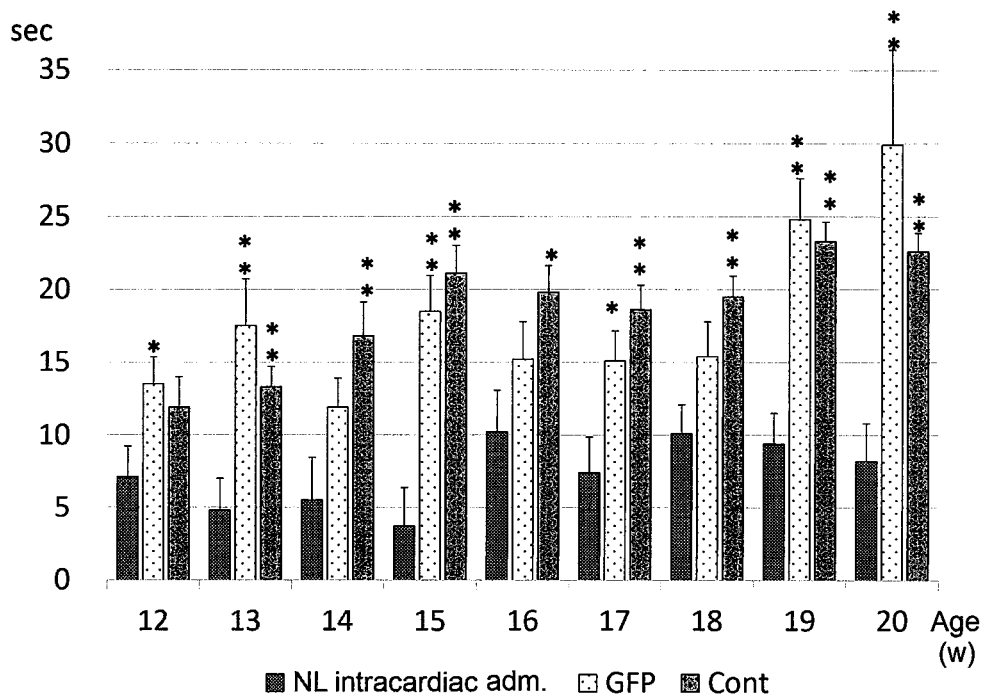
[Fig. 4]
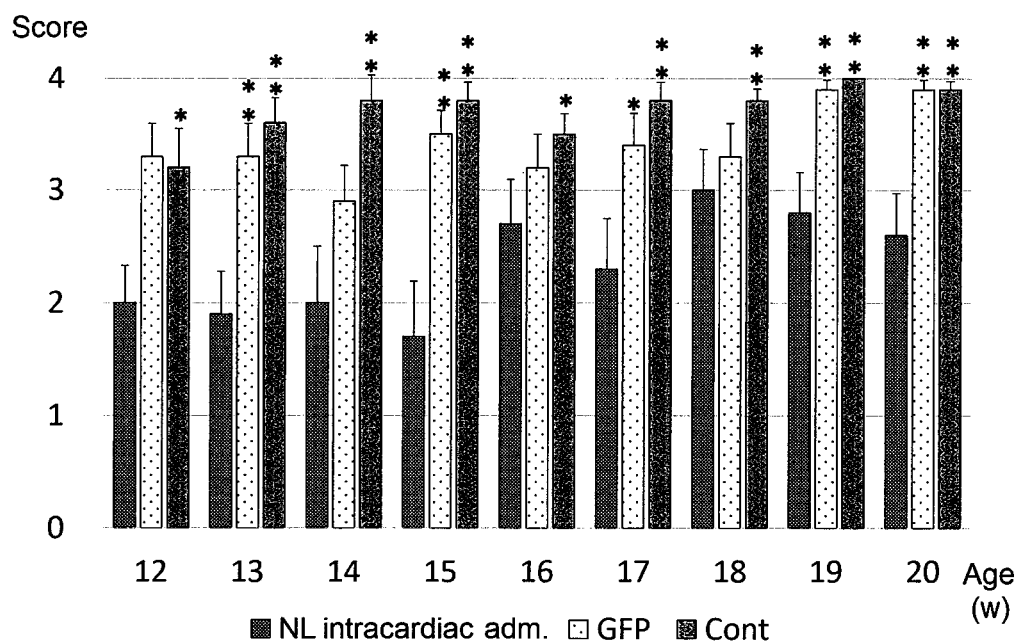

[Fig. 5]
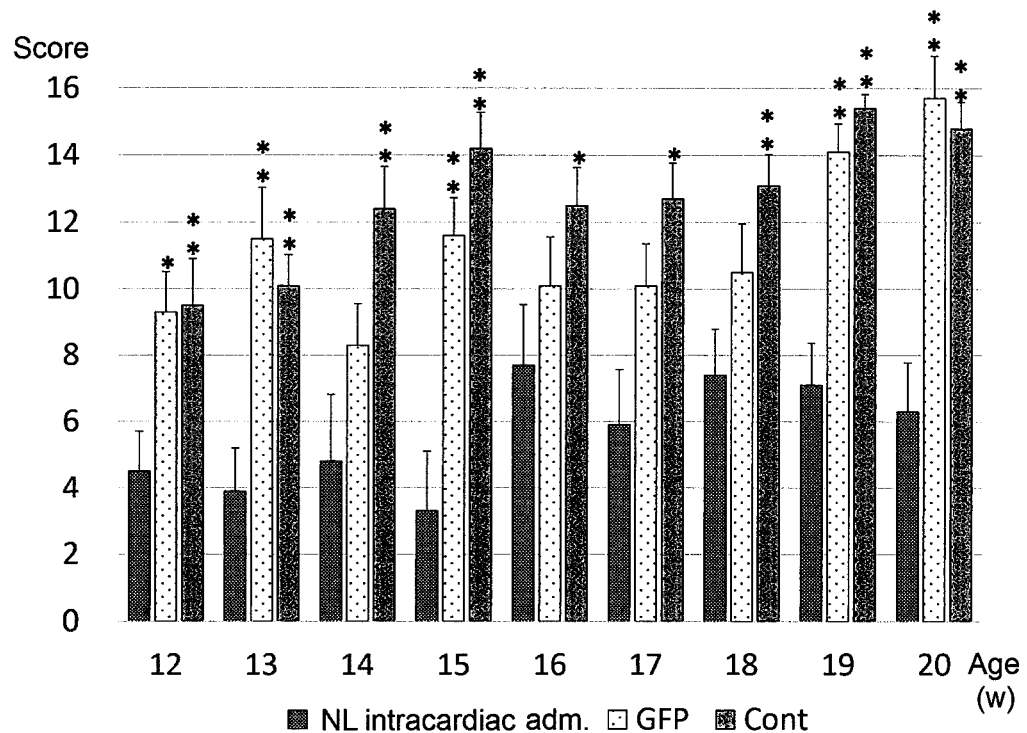
[Fig. 6]
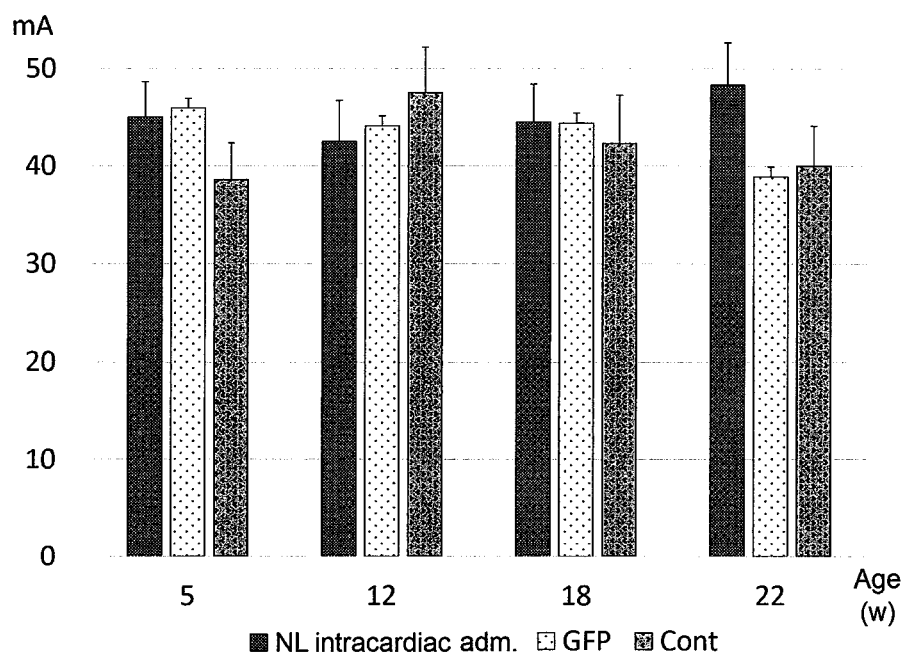

[Fig. 7]
Seizure Frequency NL2 (topical adm. to hippocampus)
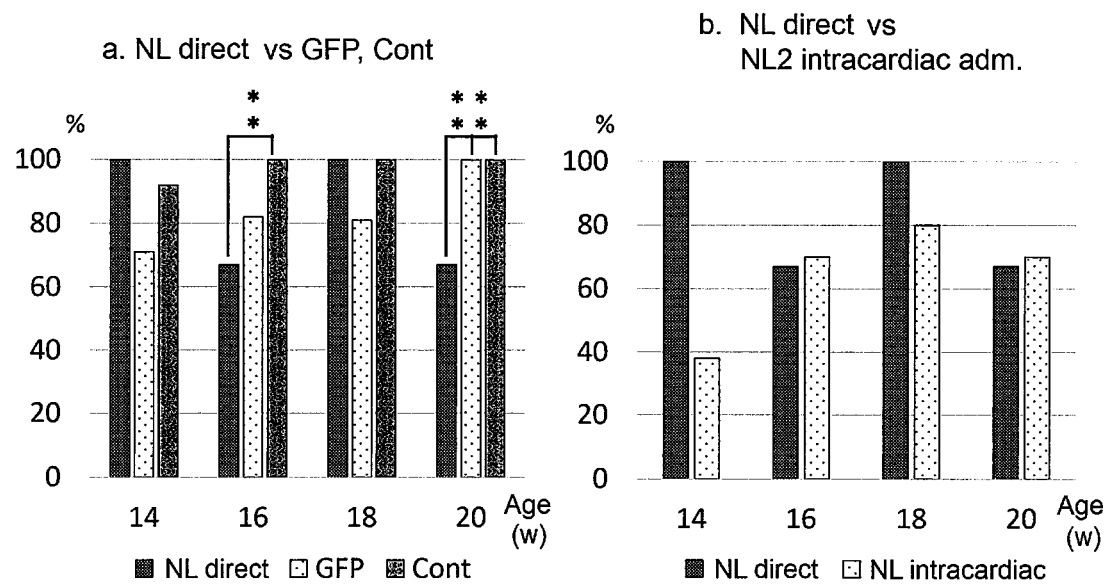
[Fig. 8]
Seizure Duration NL2 (topical adm. to hippocampus)
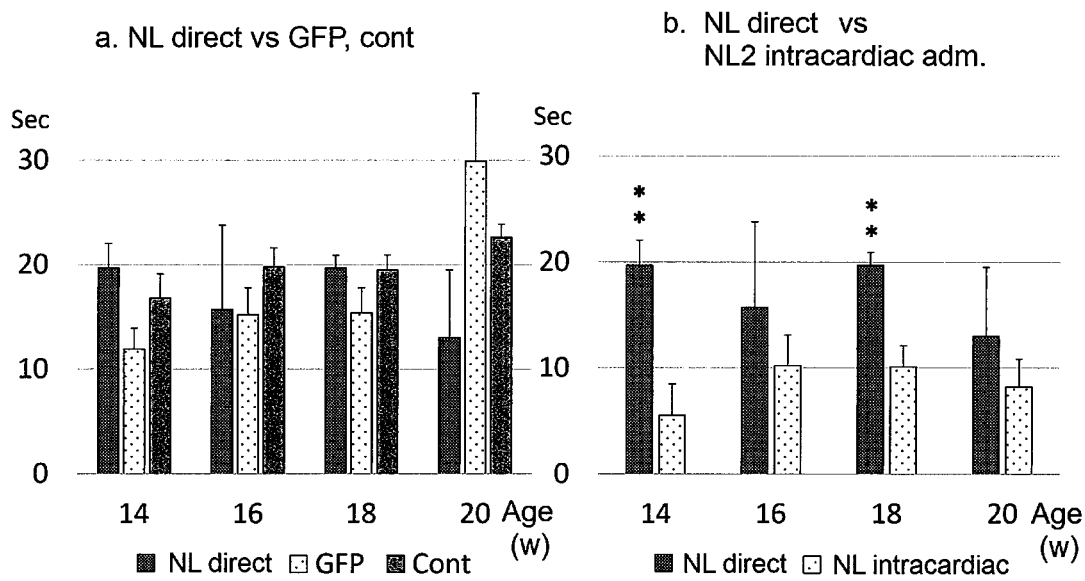

[Fig. 9]
Seizure Intensity   NL2 (topical adm. to hippocampus)
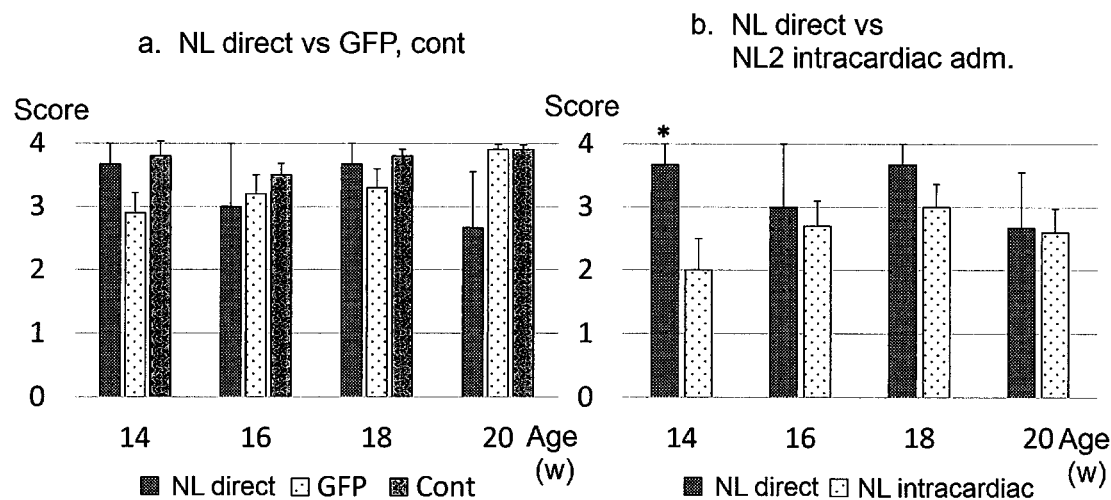
[Fig. 10]
Seizure Duration x Intensity   NL2 (topical adm. to hippocampus)
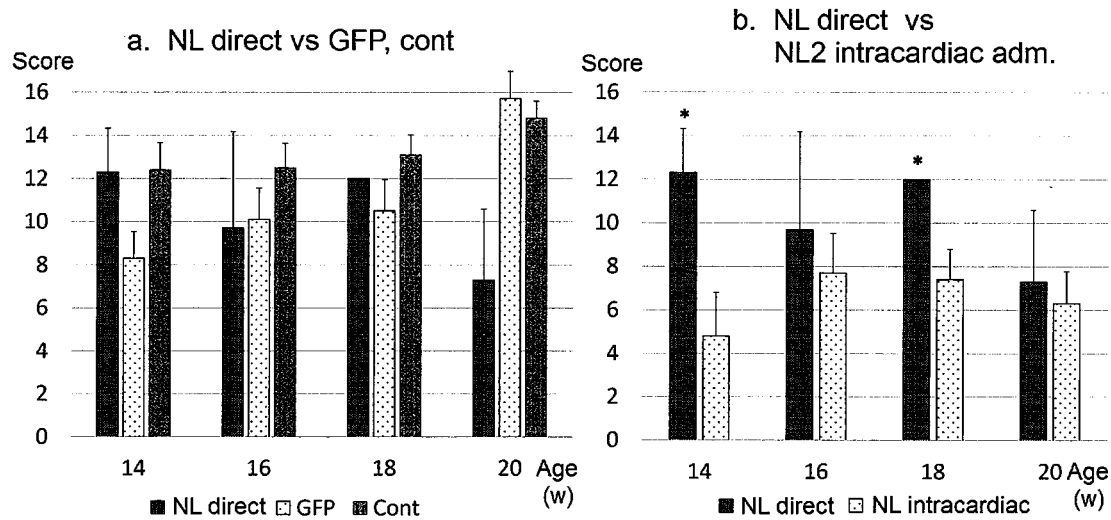

[Fig. 11]
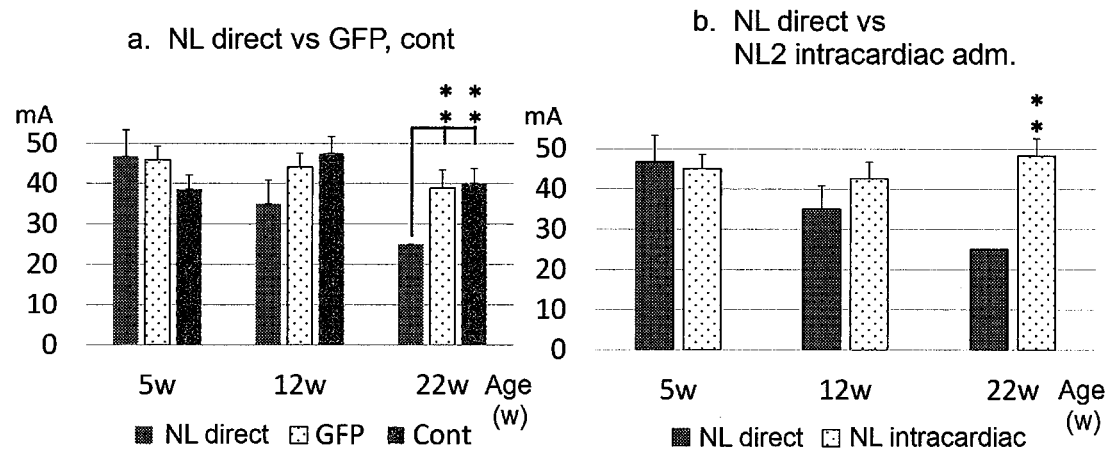

SEQUENCE LISTING

```
<160> NUMBER OF SEQ ID NOS: 11

<210> SEQ ID NO 1
<211> LENGTH: 2505
<212> TYPE: DNA
<213> ORGANISM: Homo sapiens
<220> FEATURE:
<221> NAME/KEY: CDS
<222> LOCATION: (1)..(2505)

<400> SEQUENCE: 1 atg tgg ctc ctg gcg ctg tgt ctg gtg ggg ctg gcg ggg gct caa cgc      48
Met Trp Leu Leu Ala Leu Cys Leu Val Gly Leu Ala Gly Ala Gln Arg
1               5                   10                  15 ggg gga ggg ggt ccc ggc ggc ggc gcc ccg ggc ggc ccc ggc ctg ggc      96
Gly Gly Gly Gly Pro Gly Gly Gly Ala Pro Gly Gly Pro Gly Leu Gly
                20                  25                  30 ctc ggc agc ctc ggc gag gag cgc ttc ccg gtg gtg aac acg gcc tac     144
Leu Gly Ser Leu Gly Glu Glu Arg Phe Pro Val Val Asn Thr Ala Tyr
            35                  40                  45 ggg cga gtg cgc ggt gtg cgg cgc gag ctc aac aac gag atc ctg ggc     192
Gly Arg Val Arg Gly Val Arg Arg Glu Leu Asn Asn Glu Ile Leu Gly
        50                  55                  60 ccc gtc gtg cag ttc ttg ggc gtg ccc tac gcc acg ccg ccc ctg ggc     240
Pro Val Val Gln Phe Leu Gly Val Pro Tyr Ala Thr Pro Pro Leu Gly
65                  70                  75                  80 gcc cgc cgc ttc cag ccg cct gag gcg ccc gcc tcg tgg ccc ggc gtg     288
Ala Arg Arg Phe Gln Pro Pro Glu Ala Pro Ala Ser Trp Pro Gly Val
                85                  90                  95 cgc aac gcc acc acc ctg ccg ccc gcc tgc ccg cag aac ctg cac ggg     336
Arg Asn Ala Thr Thr Leu Pro Pro Ala Cys Pro Gln Asn Leu His Gly
                100                 105                 110 gcg ctg ccc gcc atc atg ctg cct gtg tgg ttc acc gac aac ttg gag     384
```

```
                Ala Leu Pro Ala Ile Met Leu Pro Val Trp Phe Thr Asp Asn Leu Glu
                        115                 120                 125 gcg gcc gcc acc tac gtg cag aac cag agc gag gac tgc ctg tac ctc        432
Ala Ala Ala Thr Tyr Val Gln Asn Gln Ser Glu Asp Cys Leu Tyr Leu
130                 135                 140 aac ctc tac gtg ccc acc gag gac ggt ccg ctc aca aaa aaa cgt gac        480
Asn Leu Tyr Val Pro Thr Glu Asp Gly Pro Leu Thr Lys Lys Arg Asp
145                 150                 155                 160 gag gcg acg ctc aat ccg cca gac aca gat atc cgt gac cct ggg aag        528
Glu Ala Thr Leu Asn Pro Pro Asp Thr Asp Ile Arg Asp Pro Gly Lys
                165                 170                 175 aag cct gtg atg ctg ttt ctc cat ggc ggc tcc tac atg gag ggg acc        576
Lys Pro Val Met Leu Phe Leu His Gly Gly Ser Tyr Met Glu Gly Thr
        180                 185                 190 gga aac atg ttc gat ggc tca gtc ctg gct gcc tat ggc aac gtc att        624
Gly Asn Met Phe Asp Gly Ser Val Leu Ala Ala Tyr Gly Asn Val Ile
    195                 200                 205 gta gcc acg ctc aac tac cgt ctt ggg gtg ctc ggt ttt ctc agc acc        672
Val Ala Thr Leu Asn Tyr Arg Leu Gly Val Leu Gly Phe Leu Ser Thr
210                 215                 220 ggg gac cag gct gca aaa ggc aac tat ggg ctc ctg gac cag atc cag        720
Gly Asp Gln Ala Ala Lys Gly Asn Tyr Gly Leu Leu Asp Gln Ile Gln
225                 230                 235                 240 gcc ctg cgc tgg ctc agt gaa aac atc gcc cac ttt ggg ggc gac ccc        768
Ala Leu Arg Trp Leu Ser Glu Asn Ile Ala His Phe Gly Gly Asp Pro
                245                 250                 255 gag cgt atc acc atc ttt ggt tcc ggg gca ggg gcc tcc tgc gtc aac        816
Glu Arg Ile Thr Ile Phe Gly Ser Gly Ala Gly Ala Ser Cys Val Asn
            260                 265                 270 ctt ctg atc ctc tcc cac cat tca gaa ggg ctg ttc cag aag gcc atc        864
Leu Leu Ile Leu Ser His His Ser Glu Gly Leu Phe Gln Lys Ala Ile
        275                 280                 285 gcc cag agt ggc acc gcc att tcc agc tgg tct gtc aac tac cag ccg        912
Ala Gln Ser Gly Thr Ala Ile Ser Ser Trp Ser Val Asn Tyr Gln Pro
    290                 295                 300 ctc aag tac acg cgg ctg ctg gca gcc aag gtg ggc tgt gac cga gag        960
Leu Lys Tyr Thr Arg Leu Leu Ala Ala Lys Val Gly Cys Asp Arg Glu
305                 310                 315                 320 gac agc gct gaa gct gtg gag tgt ctg cgc cgg aag ccc tcc cgg gag       1008
Asp Ser Ala Glu Ala Val Glu Cys Leu Arg Arg Lys Pro Ser Arg Glu
                325                 330                 335 ctg gtg gac cag gac gtg cag cct gcc cgc tac cac atc gcc ttt ggg       1056
Leu Val Asp Gln Asp Val Gln Pro Ala Arg Tyr His Ile Ala Phe Gly
            340                 345                 350 ccc gtg gtg gat ggc gac gtg gtc ccc gat gac cct gag atc ctc atg       1104
Pro Val Val Asp Gly Asp Val Val Pro Asp Asp Pro Glu Ile Leu Met
        355                 360                 365 cag cag gga gaa ttc ctc aac tac gac atg ctc atc ggc gtc aac cag       1152
Gln Gln Gly Glu Phe Leu Asn Tyr Asp Met Leu Ile Gly Val Asn Gln
    370                 375                 380 gga gag ggc ctc aag ttc gtg gag gac tct gca gag agc gag gac ggt       1200
Gly Glu Gly Leu Lys Phe Val Glu Asp Ser Ala Glu Ser Glu Asp Gly
385                 390                 395                 400 gtg tct gcc agc gcc ttt gac ttc act gtc tcc aac ttt gtg gac aac       1248
Val Ser Ala Ser Ala Phe Asp Phe Thr Val Ser Asn Phe Val Asp Asn
                405                 410                 415 ctg tat ggc tac ccg gaa ggc aag gat gtg ctt cgg gag acc atc aag       1296
Leu Tyr Gly Tyr Pro Glu Gly Lys Asp Val Leu Arg Glu Thr Ile Lys
            420                 425                 430
```

-continued

| | | |
|---|---|---|
| ttt atg tac aca gac tgg gcc gac cgg gac aat ggc gaa atg cgc cgc<br>Phe Met Tyr Thr Asp Trp Ala Asp Arg Asp Asn Gly Glu Met Arg Arg<br>              435                    440                    445 | 1344 |
| aaa acc ctg ctg gcg ctc ttt act gac cac caa tgg gtg gca cca gct<br>Lys Thr Leu Leu Ala Leu Phe Thr Asp His Gln Trp Val Ala Pro Ala<br>450                    455                    460 | 1392 |
| gtg gcc act gcc aag ctg cac gcc gac tac cag tct ccc gtc tac ttt<br>Val Ala Thr Ala Lys Leu His Ala Asp Tyr Gln Ser Pro Val Tyr Phe<br>465                    470                    475                    480 | 1440 |
| tac acc ttc tac cac cac tgc cag gcg gag ggc cgg cct gag tgg gca<br>Tyr Thr Phe Tyr His His Cys Gln Ala Glu Gly Arg Pro Glu Trp Ala<br>              485                    490                    495 | 1488 |
| gat gcg gcg cac ggg gat gaa ctg ccc tat gtc ttt ggc gtg ccc atg<br>Asp Ala Ala His Gly Asp Glu Leu Pro Tyr Val Phe Gly Val Pro Met<br>                  500                    505                    510 | 1536 |
| gtg ggt gcc acc gac ctc ttc ccc tgt aac ttc tcc aag aat gac gtc<br>Val Gly Ala Thr Asp Leu Phe Pro Cys Asn Phe Ser Lys Asn Asp Val<br>              515                    520                    525 | 1584 |
| atg ctc agt gcc gtg gtc atg acc tac tgg acc aac ttc gcc aag act<br>Met Leu Ser Ala Val Val Met Thr Tyr Trp Thr Asn Phe Ala Lys Thr<br>530                    535                    540 | 1632 |
| ggg gac ccc aac cag ccg gtg ccg cag gat acc aag ttc atc cac acc<br>Gly Asp Pro Asn Gln Pro Val Pro Gln Asp Thr Lys Phe Ile His Thr<br>545                    550                    555                    560 | 1680 |
| aag ccc aat cgc ttc gag gag gtg gtg tgg agc aaa ttc aac agc aag<br>Lys Pro Asn Arg Phe Glu Glu Val Val Trp Ser Lys Phe Asn Ser Lys<br>                  565                    570                    575 | 1728 |
| gag aag cag tat ctg cac ata ggc ctg aag cca cgc gtg cgt gac aac<br>Glu Lys Gln Tyr Leu His Ile Gly Leu Lys Pro Arg Val Arg Asp Asn<br>              580                    585                    590 | 1776 |
| tac cgc gcc aac aag gtg gcc ttc tgg ctg gag ctc gtg ccc cac ctg<br>Tyr Arg Ala Asn Lys Val Ala Phe Trp Leu Glu Leu Val Pro His Leu<br>595                    600                    605 | 1824 |
| cac aac ctg cac acg gag ctc ttc acc acc acc cgc ctg cct ccc<br>His Asn Leu His Thr Glu Leu Phe Thr Thr Thr Arg Leu Pro Pro<br>              610                    615                    620 | 1872 |
| tac gcc acg cgc tgg ccg cct cgt ccc ccc gct ggc gcc ccg ggc aca<br>Tyr Ala Thr Arg Trp Pro Pro Arg Pro Pro Ala Gly Ala Pro Gly Thr<br>625                    630                    635                    640 | 1920 |
| cgc cgg ccc ccg ccg cct gcc acc ctg cct ccc gag ccc gag ccc gag<br>Arg Arg Pro Pro Pro Pro Ala Thr Leu Pro Pro Glu Pro Glu Pro Glu<br>                  645                    650                    655 | 1968 |
| ccc ggc cca agg gcc tat gac cgc ttc ccc ggg gac tca cgg gac tac<br>Pro Gly Pro Arg Ala Tyr Asp Arg Phe Pro Gly Asp Ser Arg Asp Tyr<br>              660                    665                    670 | 2016 |
| tcc acg gag ctg agc gtc acc gtg gcc gtg ggt gcc tcc ctc ctc ttc<br>Ser Thr Glu Leu Ser Val Thr Val Ala Val Gly Ala Ser Leu Leu Phe<br>675                    680                    685 | 2064 |
| ctc aac atc ctg gcc ttt gct gcc ctc tac tac aag cgg gac cgg cgg<br>Leu Asn Ile Leu Ala Phe Ala Ala Leu Tyr Tyr Lys Arg Asp Arg Arg<br>              690                    695                    700 | 2112 |
| cag gag ctg cgg tgc agg cgg ctt agc cca cct ggc ggc tca ggc tct<br>Gln Glu Leu Arg Cys Arg Arg Leu Ser Pro Pro Gly Gly Ser Gly Ser<br>705                    710                    715                    720 | 2160 |
| ggc gtg cct ggt ggg ggc ccc ctc ctc ccc gcc gcg ggc cgt gag ctg<br>Gly Val Pro Gly Gly Gly Pro Leu Leu Pro Ala Ala Gly Arg Glu Leu<br>                  725                    730                    735 | 2208 |
| cca cca gag gag gag ctg gtg tca ctg cag ctg aag cgg ggt ggt ggc<br>Pro Pro Glu Glu Glu Leu Val Ser Leu Gln Leu Lys Arg Gly Gly Gly<br>              740                    745                    750 | 2256 |

-continued

```
gtc ggg gcg gac cct gcc gag gct ctg cgc cct gcc tgc ccg ccc gac    2304
Val Gly Ala Asp Pro Ala Glu Ala Leu Arg Pro Ala Cys Pro Pro Asp
        755                 760                 765 tac acc ctg gcc ctg cgc cgg gca ccg gac gat gtg cct ctc ttg gcc    2352
Tyr Thr Leu Ala Leu Arg Arg Ala Pro Asp Asp Val Pro Leu Leu Ala
770                 775                 780 ccc ggg gcc ctg acc ctg ctg ccc agt ggc ctg ggg cca ccg cca ccc    2400
Pro Gly Ala Leu Thr Leu Leu Pro Ser Gly Leu Gly Pro Pro Pro Pro
785                 790                 795                 800 cca ccg ccc ccc tcc ctt cat ccc ttc ggg ccc ttc ccc ccg ccc cct    2448
Pro Pro Pro Pro Ser Leu His Pro Phe Gly Pro Phe Pro Pro Pro Pro
                805                 810                 815 ccc acc gcc acc agc cac aac aac acg cta ccc cac ccc cac tcc acc    2496
Pro Thr Ala Thr Ser His Asn Asn Thr Leu Pro His Pro His Ser Thr
            820                 825                 830 act cgg gta                                                        2505
Thr Arg Val
        835

<210> SEQ ID NO 2
<211> LENGTH: 835
<212> TYPE: PRT
<213> ORGANISM: Homo sapiens

<400> SEQUENCE: 2

Met Trp Leu Leu Ala Leu Cys Leu Val Gly Leu Ala Gly Ala Gln Arg
1               5                   10                  15

Gly Gly Gly Gly Pro Gly Gly Ala Pro Gly Gly Pro Gly Leu Gly
            20                  25                  30

Leu Gly Ser Leu Gly Glu Glu Arg Phe Pro Val Val Asn Thr Ala Tyr
        35                  40                  45

Gly Arg Val Arg Gly Val Arg Arg Glu Leu Asn Asn Glu Ile Leu Gly
    50                  55                  60

Pro Val Val Gln Phe Leu Gly Val Pro Tyr Ala Thr Pro Pro Leu Gly
65                  70                  75                  80

Ala Arg Arg Phe Gln Pro Pro Glu Ala Pro Ala Ser Trp Pro Gly Val
                85                  90                  95

Arg Asn Ala Thr Thr Leu Pro Pro Ala Cys Pro Gln Asn Leu His Gly
            100                 105                 110

Ala Leu Pro Ala Ile Met Leu Pro Val Trp Phe Thr Asp Asn Leu Glu
        115                 120                 125

Ala Ala Ala Thr Tyr Val Gln Asn Gln Ser Glu Asp Cys Leu Tyr Leu
    130                 135                 140

Asn Leu Tyr Val Pro Thr Glu Asp Gly Pro Leu Thr Lys Lys Arg Asp
145                 150                 155                 160

Glu Ala Thr Leu Asn Pro Pro Asp Thr Asp Ile Arg Asp Pro Gly Lys
                165                 170                 175

Lys Pro Val Met Leu Phe Leu His Gly Gly Ser Tyr Met Glu Gly Thr
            180                 185                 190

Gly Asn Met Phe Asp Gly Ser Val Leu Ala Ala Tyr Gly Asn Val Ile
        195                 200                 205

Val Ala Thr Leu Asn Tyr Arg Leu Gly Val Leu Gly Phe Leu Ser Thr
    210                 215                 220

Gly Asp Gln Ala Ala Lys Gly Asn Tyr Gly Leu Leu Asp Gln Ile Gln
225                 230                 235                 240

Ala Leu Arg Trp Leu Ser Glu Asn Ile Ala His Phe Gly Gly Asp Pro
```

```
                        245                 250                 255
Glu Arg Ile Thr Ile Phe Gly Ser Gly Ala Gly Ala Ser Cys Val Asn
                260                 265                 270

Leu Leu Ile Leu Ser His His Ser Glu Gly Leu Phe Gln Lys Ala Ile
            275                 280                 285

Ala Gln Ser Gly Thr Ala Ile Ser Ser Trp Ser Val Asn Tyr Gln Pro
        290                 295                 300

Leu Lys Tyr Thr Arg Leu Leu Ala Ala Lys Val Gly Cys Asp Arg Glu
305                 310                 315                 320

Asp Ser Ala Glu Ala Val Glu Cys Leu Arg Arg Lys Pro Ser Arg Glu
                325                 330                 335

Leu Val Asp Gln Asp Val Gln Pro Ala Arg Tyr His Ile Ala Phe Gly
            340                 345                 350

Pro Val Val Asp Gly Asp Val Val Pro Asp Asp Pro Glu Ile Leu Met
        355                 360                 365

Gln Gln Gly Glu Phe Leu Asn Tyr Asp Met Leu Ile Gly Val Asn Gln
        370                 375                 380

Gly Glu Gly Leu Lys Phe Val Glu Asp Ser Ala Glu Ser Glu Asp Gly
385                 390                 395                 400

Val Ser Ala Ser Ala Phe Asp Phe Thr Val Ser Asn Phe Val Asp Asn
                405                 410                 415

Leu Tyr Gly Tyr Pro Glu Gly Lys Asp Val Leu Arg Glu Thr Ile Lys
            420                 425                 430

Phe Met Tyr Thr Asp Trp Ala Asp Arg Asp Asn Gly Glu Met Arg Arg
        435                 440                 445

Lys Thr Leu Leu Ala Leu Phe Thr Asp His Gln Trp Val Ala Pro Ala
450                 455                 460

Val Ala Thr Ala Lys Leu His Ala Asp Tyr Gln Ser Pro Val Tyr Phe
465                 470                 475                 480

Tyr Thr Phe Tyr His His Cys Gln Ala Glu Gly Arg Pro Glu Trp Ala
                485                 490                 495

Asp Ala Ala His Gly Asp Glu Leu Pro Tyr Val Phe Gly Val Pro Met
            500                 505                 510

Val Gly Ala Thr Asp Leu Phe Pro Cys Asn Phe Ser Lys Asn Asp Val
        515                 520                 525

Met Leu Ser Ala Val Val Met Thr Tyr Trp Thr Asn Phe Ala Lys Thr
        530                 535                 540

Gly Asp Pro Asn Gln Pro Val Pro Gln Asp Thr Lys Phe Ile His Thr
545                 550                 555                 560

Lys Pro Asn Arg Phe Glu Glu Val Val Trp Ser Lys Phe Asn Ser Lys
                565                 570                 575

Glu Lys Gln Tyr Leu His Ile Gly Leu Lys Pro Arg Val Arg Asp Asn
            580                 585                 590

Tyr Arg Ala Asn Lys Val Ala Phe Trp Leu Glu Leu Val Pro His Leu
        595                 600                 605

His Asn Leu His Thr Glu Leu Phe Thr Thr Thr Arg Leu Pro Pro
        610                 615                 620

Tyr Ala Thr Arg Trp Pro Pro Arg Pro Ala Gly Ala Pro Gly Thr
625                 630                 635                 640

Arg Arg Pro Pro Pro Ala Thr Leu Pro Pro Glu Pro Glu Pro Glu
                645                 650                 655

Pro Gly Pro Arg Ala Tyr Asp Arg Phe Pro Gly Asp Ser Arg Asp Tyr
            660                 665                 670
```

-continued

```
Ser Thr Glu Leu Ser Val Thr Val Ala Val Gly Ala Ser Leu Leu Phe
        675                 680                 685

Leu Asn Ile Leu Ala Phe Ala Ala Leu Tyr Tyr Lys Arg Asp Arg Arg
        690                 695                 700

Gln Glu Leu Arg Cys Arg Arg Leu Ser Pro Pro Gly Ser Gly Ser
705                 710                 715                 720

Gly Val Pro Gly Gly Gly Pro Leu Leu Pro Ala Ala Gly Arg Glu Leu
                    725                 730                 735

Pro Pro Glu Glu Glu Leu Val Ser Leu Gln Leu Lys Arg Gly Gly Gly
                740                 745                 750

Val Gly Ala Asp Pro Ala Glu Ala Leu Arg Pro Ala Cys Pro Pro Asp
                    755                 760                 765

Tyr Thr Leu Ala Leu Arg Arg Ala Pro Asp Asp Val Pro Leu Leu Ala
                770                 775                 780

Pro Gly Ala Leu Thr Leu Leu Pro Ser Gly Leu Gly Pro Pro Pro
785                 790                 795                 800

Pro Pro Pro Pro Ser Leu His Pro Phe Gly Pro Phe Pro Pro Pro
                    805                 810                 815

Pro Thr Ala Thr Ser His Asn Asn Thr Leu Pro His Pro His Ser Thr
                820                 825                 830

Thr Arg Val
        835
```

<210> SEQ ID NO 3
<211> LENGTH: 2508
<212> TYPE: DNA
<213> ORGANISM: Mus musculus
<220> FEATURE:
<221> NAME/KEY: CDS
<222> LOCATION: (1)..(2508)

<400> SEQUENCE: 3

```
atg tgg ctc ctg gcg ttg tgt ctg gtg ggg ctg gct ggg gct caa cgg      48
Met Trp Leu Leu Ala Leu Cys Leu Val Gly Leu Ala Gly Ala Gln Arg
1               5                   10                  15 gga gga ggg ggt ccc ggc ggc ggc gcc ccg ggc ggc cca ggc ctg ggc      96
Gly Gly Gly Gly Pro Gly Gly Gly Ala Pro Gly Gly Pro Gly Leu Gly
                20                  25                  30 ctc ggc agc ctc ggg gag gag cgc ttc ccc gtg gtg aac aca gcc tac     144
Leu Gly Ser Leu Gly Glu Glu Arg Phe Pro Val Val Asn Thr Ala Tyr
            35                  40                  45 ggg cga gtg cgc ggt gtg cgg cgc gag ctc aac aac gag atc ctg ggc     192
Gly Arg Val Arg Gly Val Arg Arg Glu Leu Asn Asn Glu Ile Leu Gly
        50                  55                  60 ccg gtc gtg cag ttc ttg ggc gtg ccc tac gcc acg ccg ccc ttg ggc     240
Pro Val Val Gln Phe Leu Gly Val Pro Tyr Ala Thr Pro Pro Leu Gly
65                  70                  75                  80 gcc cgc cgc ttc cag ccg cct gag gca cct gcc tcg tgg ccc ggc gtg     288
Ala Arg Arg Phe Gln Pro Pro Glu Ala Pro Ala Ser Trp Pro Gly Val
                85                  90                  95 cgc aac gcc acc acc ctg ccg ccc gcc tgc ccg cag aac ctg cac ggg     336
Arg Asn Ala Thr Thr Leu Pro Pro Ala Cys Pro Gln Asn Leu His Gly
                100                 105                 110 gcc ctg ccg gcc atc atg ctg cct gtg tgg ttc acc gac aac ttg gag     384
Ala Leu Pro Ala Ile Met Leu Pro Val Trp Phe Thr Asp Asn Leu Glu
            115                 120                 125 gcg gcc gcc acc tac gtg cag aac cag agc gag gac tgc ctg tac ctc     432
Ala Ala Ala Thr Tyr Val Gln Asn Gln Ser Glu Asp Cys Leu Tyr Leu
```

```
                    130                 135                 140
aac ctc tac gtg ccc act gag gac ggt ccg ctc aca aaa aaa cgt gac        480
Asn Leu Tyr Val Pro Thr Glu Asp Gly Pro Leu Thr Lys Lys Arg Asp
145                 150                 155                 160 gag gcg acg ctc aat ccg cca gac aca gat atc cgg gac tct ggg aag        528
Glu Ala Thr Leu Asn Pro Pro Asp Thr Asp Ile Arg Asp Ser Gly Lys
                165                 170                 175 aaa ccg gtc atg ctg ttt cta cac ggc ggc tcc tac atg gaa ggc acc        576
Lys Pro Val Met Leu Phe Leu His Gly Gly Ser Tyr Met Glu Gly Thr
            180                 185                 190 ggg aac atg ttt gac ggc tca gtc ctg gct gcc tat ggc aat gtc atc        624
Gly Asn Met Phe Asp Gly Ser Val Leu Ala Ala Tyr Gly Asn Val Ile
        195                 200                 205 gta gta aca ctc aac tac cgt ctt ggg gtg ctc ggt ttt ctc agc act        672
Val Val Thr Leu Asn Tyr Arg Leu Gly Val Leu Gly Phe Leu Ser Thr
    210                 215                 220 ggt gac cag gct gca aaa ggc aac tat ggg ctc ctg gac cag atc cag        720
Gly Asp Gln Ala Ala Lys Gly Asn Tyr Gly Leu Leu Asp Gln Ile Gln
225                 230                 235                 240 gcc ctg cgc tgg ctc agt gaa aac att gcc cac ttt gga ggt gac cct        768
Ala Leu Arg Trp Leu Ser Glu Asn Ile Ala His Phe Gly Gly Asp Pro
                245                 250                 255 gaa cgc atc act atc ttt ggg tct ggt gca ggg gcc tcc tgt gtc aac        816
Glu Arg Ile Thr Ile Phe Gly Ser Gly Ala Gly Ala Ser Cys Val Asn
            260                 265                 270 ttg ctg atc ctt tcc cac cac tca gaa gga ctg ttc cag aag gcc att        864
Leu Leu Ile Leu Ser His His Ser Glu Gly Leu Phe Gln Lys Ala Ile
        275                 280                 285 gct caa agt ggt act gcc att tcc agc tgg tct gtc aac tac cag ccg        912
Ala Gln Ser Gly Thr Ala Ile Ser Ser Trp Ser Val Asn Tyr Gln Pro
    290                 295                 300 ctc aag tac acg cgg ctg ctg gcg gcc aaa gtg ggc tgt gac cga gaa        960
Leu Lys Tyr Thr Arg Leu Leu Ala Ala Lys Val Gly Cys Asp Arg Glu
305                 310                 315                 320 gac agc act gaa gct gtg gag tgt ctg cgc cgg aag tct tcc cgg gag       1008
Asp Ser Thr Glu Ala Val Glu Cys Leu Arg Arg Lys Ser Ser Arg Glu
                325                 330                 335 cta gtg gac cag gat gta cag cct gcc cgc tac cac att gcc ttt ggg       1056
Leu Val Asp Gln Asp Val Gln Pro Ala Arg Tyr His Ile Ala Phe Gly
            340                 345                 350 cct gtg gtg gac ggc gac gta gtc cct gat gac ccc gag atc ctc atg       1104
Pro Val Val Asp Gly Asp Val Val Pro Asp Asp Pro Glu Ile Leu Met
        355                 360                 365 caa cag ggg gaa ttc ctc aac tac gac atg ctc att ggt gtc aac cag       1152
Gln Gln Gly Glu Phe Leu Asn Tyr Asp Met Leu Ile Gly Val Asn Gln
    370                 375                 380 gga gag ggt ctc aag ttc gtg gag gac tct gca gag agt gag gac ggt       1200
Gly Glu Gly Leu Lys Phe Val Glu Asp Ser Ala Glu Ser Glu Asp Gly
385                 390                 395                 400 gtg tct gcc agc gcc ttt gac ttc acc gtc tcc aac ttt gtg gac aac       1248
Val Ser Ala Ser Ala Phe Asp Phe Thr Val Ser Asn Phe Val Asp Asn
                405                 410                 415 ttg tac ggg tac cca gaa ggc aag gac gtg ctt cga gag acc atc aag       1296
Leu Tyr Gly Tyr Pro Glu Gly Lys Asp Val Leu Arg Glu Thr Ile Lys
            420                 425                 430 ttc atg tac acg gac tgg gct gac agg gac aat ggc gag atg cgg cgg       1344
Phe Met Tyr Thr Asp Trp Ala Asp Arg Asp Asn Gly Glu Met Arg Arg
        435                 440                 445 aag acc ctg ctg gcg ctc ttt acc gac cac cag tgg gtc gcc ccg gct       1392
```

```
                                    -continued

Lys Thr Leu Leu Ala Leu Phe Thr Asp His Gln Trp Val Ala Pro Ala
    450                 455                 460 gtg gcc acc gcc aag ctg cat gcc gac tac cag tcc ccc gtc tac ttt        1440
Val Ala Thr Ala Lys Leu His Ala Asp Tyr Gln Ser Pro Val Tyr Phe
465                 470                 475                 480 tac act ttc tac cac cac tgc cag gca gag ggc cgg cca gag tgg gca        1488
Tyr Thr Phe Tyr His His Cys Gln Ala Glu Gly Arg Pro Glu Trp Ala
                485                 490                 495 gac gca gcg cac ggg gac gag ctg ccc tac gtc ttt ggt gtc ccc atg        1536
Asp Ala Ala His Gly Asp Glu Leu Pro Tyr Val Phe Gly Val Pro Met
            500                 505                 510 gtg ggc gcc act gac ctc ttc ccc tgc aac ttc tcc aag aac gat gtc        1584
Val Gly Ala Thr Asp Leu Phe Pro Cys Asn Phe Ser Lys Asn Asp Val
        515                 520                 525 atg ctc agc gca gta gtc atg acc tat tgg acc aac ttc gcc aag act        1632
Met Leu Ser Ala Val Val Met Thr Tyr Trp Thr Asn Phe Ala Lys Thr
    530                 535                 540 ggt gac ccc aac cag cct gtg cca cag gac acc aag ttc atc cac acc        1680
Gly Asp Pro Asn Gln Pro Val Pro Gln Asp Thr Lys Phe Ile His Thr
545                 550                 555                 560 aag ccc aac cgc ttt gaa gag gta gtg tgg agc aag ttc aac agc aag        1728
Lys Pro Asn Arg Phe Glu Glu Val Val Trp Ser Lys Phe Asn Ser Lys
                565                 570                 575 gaa aag cag tat ctg cac ata ggc ttg aaa cca cgc gtg cgc gac aac        1776
Glu Lys Gln Tyr Leu His Ile Gly Leu Lys Pro Arg Val Arg Asp Asn
            580                 585                 590 tac cgt gcc aac aag gtg gcc ttc tgg ctg gag ctc gtg ccc cac ctg        1824
Tyr Arg Ala Asn Lys Val Ala Phe Trp Leu Glu Leu Val Pro His Leu
        595                 600                 605 cac aac ctg cac aca gag ctc ttc acc acc acc act cgc ctg cct ccc        1872
His Asn Leu His Thr Glu Leu Phe Thr Thr Thr Thr Arg Leu Pro Pro
    610                 615                 620 tat gcc aca cgc tgg cca cct cgc aca cct ggt cct ggc act tcc ggc        1920
Tyr Ala Thr Arg Trp Pro Pro Arg Thr Pro Gly Pro Gly Thr Ser Gly
625                 630                 635                 640 aca cgc cgt cct ccc cca cct gcc act ctg cca cct gag tct gat att        1968
Thr Arg Arg Pro Pro Pro Ala Thr Leu Pro Pro Glu Ser Asp Ile
                645                 650                 655 gac cta ggc cca agg gcc tat gac cgc ttc ccc ggt gac tcg agg gac        2016
Asp Leu Gly Pro Arg Ala Tyr Asp Arg Phe Pro Gly Asp Ser Arg Asp
            660                 665                 670 tac tcc acg gag cta agc gtg act gtg gca gtg ggt gcc tcc ctc ctc        2064
Tyr Ser Thr Glu Leu Ser Val Thr Val Ala Val Gly Ala Ser Leu Leu
        675                 680                 685 ttc ctc aac atc ctt gcc ttt gcc gcc ctc tat tac aag cgg gac cgg        2112
Phe Leu Asn Ile Leu Ala Phe Ala Ala Leu Tyr Tyr Lys Arg Asp Arg
    690                 695                 700 cgc cag gag ctg cgg tgc cgg agg ctt agc cca cca gga ggc tca ggc        2160
Arg Gln Glu Leu Arg Cys Arg Arg Leu Ser Pro Pro Gly Gly Ser Gly
705                 710                 715                 720 tca ggt gtg cct ggt ggg ggc ccc ctg ctt ccc act gct ggc cgt gag        2208
Ser Gly Val Pro Gly Gly Gly Pro Leu Leu Pro Thr Ala Gly Arg Glu
                725                 730                 735 cta ccc ccg gag gag gag cta gta tcg ctg cag ctg aag cgg ggt ggt        2256
Leu Pro Pro Glu Glu Glu Leu Val Ser Leu Gln Leu Lys Arg Gly Gly
            740                 745                 750 ggt gtt ggg gcg gac cct gct gag gcc ctg cgc cct gcc tgt cca ccc        2304
Gly Val Gly Ala Asp Pro Ala Glu Ala Leu Arg Pro Ala Cys Pro Pro
        755                 760                 765
```

```
gac tat acc ctg gcc ttg cgc cgg gca ccg gac gat gtg cct ctc ttg     2352
Asp Tyr Thr Leu Ala Leu Arg Arg Ala Pro Asp Asp Val Pro Leu Leu
770                 775                 780 gcc ccc ggg gcc cta acc ctg ctg cct agt ggc ctg ggg ccc ccg ccc     2400
Ala Pro Gly Ala Leu Thr Leu Leu Pro Ser Gly Leu Gly Pro Pro Pro
785                 790                 795                 800 ccg ccc cca ccc cct tct ctc cat ccc ttt ggg ccc ttc cca ccc cca     2448
Pro Pro Pro Pro Pro Ser Leu His Pro Phe Gly Pro Phe Pro Pro Pro
                805                 810                 815 ccc cct act gct acc agc cac aac aac acg cta ccc cat ccc cac tcc     2496
Pro Pro Thr Ala Thr Ser His Asn Asn Thr Leu Pro His Pro His Ser
                820                 825                 830 acc act cgg gta                                                     2508
Thr Thr Arg Val
        835

<210> SEQ ID NO 4
<211> LENGTH: 836
<212> TYPE: PRT
<213> ORGANISM: Mus musculus

<400> SEQUENCE: 4

Met Trp Leu Leu Ala Leu Cys Leu Val Gly Leu Ala Gly Ala Gln Arg
1               5                   10                  15

Gly Gly Gly Gly Pro Gly Gly Gly Ala Pro Gly Gly Pro Gly Leu Gly
                20                  25                  30

Leu Gly Ser Leu Gly Glu Glu Arg Phe Pro Val Val Asn Thr Ala Tyr
            35                  40                  45

Gly Arg Val Arg Gly Val Arg Arg Glu Leu Asn Asn Glu Ile Leu Gly
        50                  55                  60

Pro Val Val Gln Phe Leu Gly Val Pro Tyr Ala Thr Pro Pro Leu Gly
65                  70                  75                  80

Ala Arg Arg Phe Gln Pro Pro Glu Ala Pro Ala Ser Trp Pro Gly Val
                85                  90                  95

Arg Asn Ala Thr Thr Leu Pro Pro Ala Cys Pro Gln Asn Leu His Gly
                100                 105                 110

Ala Leu Pro Ala Ile Met Leu Pro Val Trp Phe Thr Asp Asn Leu Glu
            115                 120                 125

Ala Ala Ala Thr Tyr Val Gln Asn Gln Ser Glu Asp Cys Leu Tyr Leu
        130                 135                 140

Asn Leu Tyr Val Pro Thr Glu Asp Gly Pro Leu Thr Lys Lys Arg Asp
145                 150                 155                 160

Glu Ala Thr Leu Asn Pro Pro Asp Thr Asp Ile Arg Asp Ser Gly Lys
                165                 170                 175

Lys Pro Val Met Leu Phe Leu His Gly Gly Ser Tyr Met Glu Gly Thr
            180                 185                 190

Gly Asn Met Phe Asp Gly Ser Val Leu Ala Ala Tyr Gly Asn Val Ile
        195                 200                 205

Val Val Thr Leu Asn Tyr Arg Leu Gly Val Leu Gly Phe Leu Ser Thr
        210                 215                 220

Gly Asp Gln Ala Ala Lys Gly Asn Tyr Gly Leu Leu Asp Gln Ile Gln
225                 230                 235                 240

Ala Leu Arg Trp Leu Ser Glu Asn Ile Ala His Phe Gly Gly Asp Pro
                245                 250                 255

Glu Arg Ile Thr Ile Phe Gly Ser Gly Ala Gly Ala Ser Cys Val Asn
            260                 265                 270
```

```
Leu Leu Ile Leu Ser His His Ser Glu Gly Leu Phe Gln Lys Ala Ile
            275                 280                 285
Ala Gln Ser Gly Thr Ala Ile Ser Ser Trp Ser Val Asn Tyr Gln Pro
        290                 295                 300
Leu Lys Tyr Thr Arg Leu Leu Ala Ala Lys Val Gly Cys Asp Arg Glu
305                 310                 315                 320
Asp Ser Thr Glu Ala Val Glu Cys Leu Arg Arg Lys Ser Ser Arg Glu
                325                 330                 335
Leu Val Asp Gln Asp Val Gln Pro Ala Arg Tyr His Ile Ala Phe Gly
            340                 345                 350
Pro Val Val Asp Gly Asp Val Val Pro Asp Pro Glu Ile Leu Met
        355                 360                 365
Gln Gln Gly Glu Phe Leu Asn Tyr Asp Met Leu Ile Gly Val Asn Gln
    370                 375                 380
Gly Glu Gly Leu Lys Phe Val Glu Asp Ser Ala Glu Ser Glu Asp Gly
385                 390                 395                 400
Val Ser Ala Ser Ala Phe Asp Phe Thr Val Ser Asn Phe Val Asp Asn
                405                 410                 415
Leu Tyr Gly Tyr Pro Glu Gly Lys Asp Val Leu Arg Glu Thr Ile Lys
            420                 425                 430
Phe Met Tyr Thr Asp Trp Ala Asp Arg Asp Asn Gly Glu Met Arg Arg
        435                 440                 445
Lys Thr Leu Leu Ala Leu Phe Thr Asp His Gln Trp Val Ala Pro Ala
    450                 455                 460
Val Ala Thr Ala Lys Leu His Ala Asp Tyr Gln Ser Pro Val Tyr Phe
465                 470                 475                 480
Tyr Thr Phe Tyr His His Cys Gln Ala Glu Gly Arg Pro Glu Trp Ala
                485                 490                 495
Asp Ala Ala His Gly Asp Glu Leu Pro Tyr Val Phe Gly Val Pro Met
            500                 505                 510
Val Gly Ala Thr Asp Leu Phe Pro Cys Asn Phe Ser Lys Asn Asp Val
        515                 520                 525
Met Leu Ser Ala Val Val Met Thr Tyr Trp Thr Asn Phe Ala Lys Thr
    530                 535                 540
Gly Asp Pro Asn Gln Pro Val Pro Gln Asp Thr Lys Phe Ile His Thr
545                 550                 555                 560
Lys Pro Asn Arg Phe Glu Glu Val Val Trp Ser Lys Phe Asn Ser Lys
                565                 570                 575
Glu Lys Gln Tyr Leu His Ile Gly Leu Lys Pro Arg Val Arg Asp Asn
            580                 585                 590
Tyr Arg Ala Asn Lys Val Ala Phe Trp Leu Glu Leu Val Pro His Leu
        595                 600                 605
His Asn Leu His Thr Glu Leu Phe Thr Thr Thr Arg Leu Pro Pro
    610                 615                 620
Tyr Ala Thr Arg Trp Pro Pro Arg Thr Pro Gly Pro Gly Thr Ser Gly
625                 630                 635                 640
Thr Arg Arg Pro Pro Pro Ala Thr Leu Pro Pro Glu Ser Asp Ile
                645                 650                 655
Asp Leu Gly Pro Arg Ala Tyr Asp Arg Phe Pro Gly Asp Ser Arg Asp
            660                 665                 670
Tyr Ser Thr Glu Leu Ser Val Thr Val Ala Val Gly Ala Ser Leu Leu
        675                 680                 685
Phe Leu Asn Ile Leu Ala Phe Ala Ala Leu Tyr Tyr Lys Arg Asp Arg
```

```
            690                 695                 700
Arg Gln Glu Leu Arg Cys Arg Arg Leu Ser Pro Pro Gly Gly Ser Gly
705                 710                 715                 720

Ser Gly Val Pro Gly Gly Pro Leu Leu Pro Thr Ala Gly Arg Glu
                725                 730                 735

Leu Pro Pro Glu Glu Leu Val Ser Leu Gln Leu Lys Arg Gly Gly
                740                 745                 750

Gly Val Gly Ala Asp Pro Ala Glu Ala Leu Arg Pro Ala Cys Pro Pro
                755                 760                 765

Asp Tyr Thr Leu Ala Leu Arg Arg Ala Pro Asp Val Pro Leu Leu
        770                 775                 780

Ala Pro Gly Ala Leu Thr Leu Leu Pro Ser Gly Leu Gly Pro Pro Pro
785                 790                 795                 800

Pro Pro Pro Pro Pro Ser Leu His Pro Phe Gly Phe Pro Pro Pro
                805                 810                 815

Pro Pro Thr Ala Thr Ser His Asn Asn Thr Leu Pro His Pro His Ser
                820                 825                 830

Thr Thr Arg Val
        835

<210> SEQ ID NO 5
<211> LENGTH: 2508
<212> TYPE: DNA
<213> ORGANISM: Rattus norvegicus
<220> FEATURE:
<221> NAME/KEY: CDS
<222> LOCATION: (1)..(2508)

<400> SEQUENCE: 5 atg tgg ctc ctg gcg ttg tgt ctg gtg ggg ctg gct ggg gct caa cgg     48
Met Trp Leu Leu Ala Leu Cys Leu Val Gly Leu Ala Gly Ala Gln Arg
1               5                   10                  15 gga gga ggg ggt ccc ggc ggc ggc gcc ccg ggc ggc cca ggc ctg ggc     96
Gly Gly Gly Gly Pro Gly Gly Gly Ala Pro Gly Gly Pro Gly Leu Gly
                20                  25                  30 ctc ggc agc ctc ggg gag gag cgc ttc ccg gtg gtg aac aca gcc tac    144
Leu Gly Ser Leu Gly Glu Glu Arg Phe Pro Val Val Asn Thr Ala Tyr
            35                  40                  45 ggg cga gtg cgc ggt gtg cgg cgc gag ctc aac aac gag atc ctg ggc    192
Gly Arg Val Arg Gly Val Arg Arg Glu Leu Asn Asn Glu Ile Leu Gly
        50                  55                  60 ccg gtc gtg cag ttc ttg ggc gtg ccc tac gcc acg ccg ccc ttg ggc    240
Pro Val Val Gln Phe Leu Gly Val Pro Tyr Ala Thr Pro Pro Leu Gly
65                  70                  75                  80 gcc cgc cgc ttc cag ccg cct gag gca cct gcc tcg tgg ccc ggc gtg    288
Ala Arg Arg Phe Gln Pro Pro Glu Ala Pro Ala Ser Trp Pro Gly Val
                85                  90                  95 cgc aac gcc acc acc ctg ccg ccc gcc tgc ccg cag aac ctg cac ggg    336
Arg Asn Ala Thr Thr Leu Pro Pro Ala Cys Pro Gln Asn Leu His Gly
            100                 105                 110 gcc ctg ccg gcc atc atg ctg cct gtg tgg ttc acc gac aac ttg gag    384
Ala Leu Pro Ala Ile Met Leu Pro Val Trp Phe Thr Asp Asn Leu Glu
        115                 120                 125 gcg gcc gcc acc tac gtg cag aac cag agc gag gac tgc ctg tac ctc    432
Ala Ala Ala Thr Tyr Val Gln Asn Gln Ser Glu Asp Cys Leu Tyr Leu
    130                 135                 140 aac ctc tac gtg ccc act gag gac ggt ccg ctc aca aaa aaa cgt gac    480
Asn Leu Tyr Val Pro Thr Glu Asp Gly Pro Leu Thr Lys Lys Arg Asp
145                 150                 155                 160
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gag | gcg | acg | ctc | aat | ccg | cca | gac | aca | gat | atc | cgg | gac | tct | ggg | aag | 528  |
| Glu | Ala | Thr | Leu | Asn | Pro | Pro | Asp | Thr | Asp | Ile | Arg | Asp | Ser | Gly | Lys |      |
|     |     |     |     | 165 |     |     |     | 170 |     |     |     | 175 |     |     |     |      |
| aaa | cca | gtc | atg | ctg | ttt | cta | cac | ggc | ggc | tcc | tac | atg | gag | ggc | acc | 576  |
| Lys | Pro | Val | Met | Leu | Phe | Leu | His | Gly | Gly | Ser | Tyr | Met | Glu | Gly | Thr |      |
|     |     | 180 |     |     |     |     | 185 |     |     |     |     | 190 |     |     |     |      |
| ggg | aac | atg | ttc | gac | ggc | tca | gtc | ctg | gct | gcc | tat | ggc | aat | gtc | atc | 624  |
| Gly | Asn | Met | Phe | Asp | Gly | Ser | Val | Leu | Ala | Ala | Tyr | Gly | Asn | Val | Ile |      |
| 195 |     |     |     |     | 200 |     |     |     |     | 205 |     |     |     |     |     |      |
| gta | gcc | aca | ctc | aac | tac | cgt | ctt | ggg | gtg | ctc | ggc | ttt | ctc | agc | act | 672  |
| Val | Ala | Thr | Leu | Asn | Tyr | Arg | Leu | Gly | Val | Leu | Gly | Phe | Leu | Ser | Thr |      |
|     | 210 |     |     |     |     | 215 |     |     |     |     | 220 |     |     |     |     |      |
| ggt | gac | cag | gct | gca | aaa | ggc | aac | tac | ggg | ctc | ctg | gac | cag | atc | cag | 720  |
| Gly | Asp | Gln | Ala | Ala | Lys | Gly | Asn | Tyr | Gly | Leu | Leu | Asp | Gln | Ile | Gln |      |
| 225 |     |     |     |     | 230 |     |     |     |     | 235 |     |     |     |     | 240 |      |
| gcc | ctg | cgc | tgg | ctc | agt | gaa | aac | att | gcc | cac | ttt | ggc | ggt | gac | cct | 768  |
| Ala | Leu | Arg | Trp | Leu | Ser | Glu | Asn | Ile | Ala | His | Phe | Gly | Gly | Asp | Pro |      |
|     |     |     |     | 245 |     |     |     |     | 250 |     |     |     |     | 255 |     |      |
| gaa | cgc | atc | acc | atc | ttt | ggg | tct | ggt | gcg | ggg | gcc | tcc | tgt | gtc | aac | 816  |
| Glu | Arg | Ile | Thr | Ile | Phe | Gly | Ser | Gly | Ala | Gly | Ala | Ser | Cys | Val | Asn |      |
|     |     |     | 260 |     |     |     |     | 265 |     |     |     |     | 270 |     |     |      |
| ttg | ctg | atc | ctc | tcc | cac | cat | tca | gaa | ggg | ctg | ttc | cag | aag | gcc | att | 864  |
| Leu | Leu | Ile | Leu | Ser | His | His | Ser | Glu | Gly | Leu | Phe | Gln | Lys | Ala | Ile |      |
|     | 275 |     |     |     |     | 280 |     |     |     |     | 285 |     |     |     |     |      |
| gct | cag | agt | ggc | act | gcc | att | tcc | agc | tgg | tct | gtc | aac | tac | cag | ccg | 912  |
| Ala | Gln | Ser | Gly | Thr | Ala | Ile | Ser | Ser | Trp | Ser | Val | Asn | Tyr | Gln | Pro |      |
| 290 |     |     |     |     | 295 |     |     |     |     | 300 |     |     |     |     |     |      |
| ctc | aag | tac | acg | cgg | ctg | ctg | gca | gcc | aaa | gtg | ggc | tgt | gac | cga | gag | 960  |
| Leu | Lys | Tyr | Thr | Arg | Leu | Leu | Ala | Ala | Lys | Val | Gly | Cys | Asp | Arg | Glu |      |
| 305 |     |     |     |     | 310 |     |     |     |     | 315 |     |     |     |     | 320 |      |
| gac | agc | acg | gaa | gct | gtg | gaa | tgt | cta | cgc | cgg | aag | tct | tcc | cgg | gag | 1008 |
| Asp | Ser | Thr | Glu | Ala | Val | Glu | Cys | Leu | Arg | Arg | Lys | Ser | Ser | Arg | Glu |      |
|     |     |     |     | 325 |     |     |     |     | 330 |     |     |     |     | 335 |     |      |
| cta | gta | gac | cag | gat | gtg | cag | cct | gcc | cgc | tac | cac | att | gcc | ttt | ggg | 1056 |
| Leu | Val | Asp | Gln | Asp | Val | Gln | Pro | Ala | Arg | Tyr | His | Ile | Ala | Phe | Gly |      |
|     |     |     | 340 |     |     |     |     | 345 |     |     |     |     | 350 |     |     |      |
| cct | gtg | gtg | gac | ggc | gat | gta | gtc | cct | gat | gac | cct | gag | atc | ctc | atg | 1104 |
| Pro | Val | Val | Asp | Gly | Asp | Val | Val | Pro | Asp | Asp | Pro | Glu | Ile | Leu | Met |      |
|     |     | 355 |     |     |     |     | 360 |     |     |     |     | 365 |     |     |     |      |
| caa | cag | gga | gaa | ttc | ctc | aac | tac | gac | atg | ctc | att | ggc | gtc | aac | cag | 1152 |
| Gln | Gln | Gly | Glu | Phe | Leu | Asn | Tyr | Asp | Met | Leu | Ile | Gly | Val | Asn | Gln |      |
| 370 |     |     |     |     | 375 |     |     |     |     | 380 |     |     |     |     |     |      |
| gga | gag | ggt | ctc | aag | ttc | gtg | gag | gac | tct | gca | gag | agt | gag | gac | ggg | 1200 |
| Gly | Glu | Gly | Leu | Lys | Phe | Val | Glu | Asp | Ser | Ala | Glu | Ser | Glu | Asp | Gly |      |
| 385 |     |     |     |     | 390 |     |     |     |     | 395 |     |     |     |     | 400 |      |
| gtg | tct | gcc | agc | gcc | ttt | gac | ttc | act | gtc | tcc | aac | ttt | gtg | gac | aac | 1248 |
| Val | Ser | Ala | Ser | Ala | Phe | Asp | Phe | Thr | Val | Ser | Asn | Phe | Val | Asp | Asn |      |
|     |     |     |     | 405 |     |     |     |     | 410 |     |     |     |     | 415 |     |      |
| ttg | tat | ggg | tat | cca | gag | ggc | aag | gat | gtg | ctt | cga | gag | acc | atc | aag | 1296 |
| Leu | Tyr | Gly | Tyr | Pro | Glu | Gly | Lys | Asp | Val | Leu | Arg | Glu | Thr | Ile | Lys |      |
|     |     |     | 420 |     |     |     |     | 425 |     |     |     |     | 430 |     |     |      |
| ttc | atg | tac | acg | gac | tgg | gct | gac | cgg | gac | aat | ggc | gag | atg | cgg | cgt | 1344 |
| Phe | Met | Tyr | Thr | Asp | Trp | Ala | Asp | Arg | Asp | Asn | Gly | Glu | Met | Arg | Arg |      |
|     |     |     | 435 |     |     |     |     | 440 |     |     |     |     | 445 |     |     |      |
| aag | acc | ctg | ttg | gca | ctc | ttt | act | gac | cac | cag | tgg | gta | gcc | cca | gct | 1392 |
| Lys | Thr | Leu | Leu | Ala | Leu | Phe | Thr | Asp | His | Gln | Trp | Val | Ala | Pro | Ala |      |
| 450 |     |     |     |     | 455 |     |     |     |     | 460 |     |     |     |     |     |      |
| gtg | gcc | act | gcc | aag | cta | cat | gct | gac | tac | cag | tcc | cct | gtc | tac | ttt | 1440 |
| Val | Ala | Thr | Ala | Lys | Leu | His | Ala | Asp | Tyr | Gln | Ser | Pro | Val | Tyr | Phe |      |

-continued

| | | | | |
|---|---|---|---|---|
| 465 | 470 | 475 | 480 | |
| tac act ttt tac cac cac tgc cag gct gag ggc cgg cca gag tgg gca<br>Tyr Thr Phe Tyr His His Cys Gln Ala Glu Gly Arg Pro Glu Trp Ala<br>                      485                      490                  495 | | | | 1488 |
| gat gca gcg cat ggg gat gag ctg ccc tac gtc ttt ggt gtg ccc atg<br>Asp Ala Ala His Gly Asp Glu Leu Pro Tyr Val Phe Gly Val Pro Met<br>            500                      505                      510 | | | | 1536 |
| gtg ggc gcc acc gac ctc ttc ccc tgc aac ttc tcc aag aat gat gtc<br>Val Gly Ala Thr Asp Leu Phe Pro Cys Asn Phe Ser Lys Asn Asp Val<br>            515                      520                      525 | | | | 1584 |
| atg ctc agc gca gta gtc atg acc tac tgg acc aac ttc gcc aag act<br>Met Leu Ser Ala Val Val Met Thr Tyr Trp Thr Asn Phe Ala Lys Thr<br>530                      535                      540 | | | | 1632 |
| ggt gac ccc aac cag cct gtg cca cag gac acc aag ttc atc cac acc<br>Gly Asp Pro Asn Gln Pro Val Pro Gln Asp Thr Lys Phe Ile His Thr<br>545                      550                      555                      560 | | | | 1680 |
| aag ccc aac cgc ttt gaa gag gtg gta tgg agc aag ttc aac agc aag<br>Lys Pro Asn Arg Phe Glu Glu Val Val Trp Ser Lys Phe Asn Ser Lys<br>                      565                      570                      575 | | | | 1728 |
| gaa aag cag tac ctg cac ata ggc ttg aaa cca cgc gtg cgt gac aac<br>Glu Lys Gln Tyr Leu His Ile Gly Leu Lys Pro Arg Val Arg Asp Asn<br>                580                      585                      590 | | | | 1776 |
| tac cgt gcc aac aag gtg gcc ttc tgg ctg gag ctc gtg ccc cac ctg<br>Tyr Arg Ala Asn Lys Val Ala Phe Trp Leu Glu Leu Val Pro His Leu<br>            595                      600                      605 | | | | 1824 |
| cac aac ctg cac aca gag ctc ttc acc acc acc act cgc ctg cct ccc<br>His Asn Leu His Thr Glu Leu Phe Thr Thr Thr Thr Arg Leu Pro Pro<br>        610                      615                      620 | | | | 1872 |
| tac gcc aca cgc tgg cca cct cgc aca ccg ggt cct ggc act tcc ggc<br>Tyr Ala Thr Arg Trp Pro Pro Arg Thr Pro Gly Pro Gly Thr Ser Gly<br>625                      630                      635                      640 | | | | 1920 |
| aca cgc cgt cct ccc cca ccc gcc act ctg cca cct gag tct gat att<br>Thr Arg Arg Pro Pro Pro Pro Ala Thr Leu Pro Pro Glu Ser Asp Ile<br>                      645                      650                      655 | | | | 1968 |
| gac ctg ggc cca agg gcc tat gac cgc ttc ccc ggt gac tcg agg gac<br>Asp Leu Gly Pro Arg Ala Tyr Asp Arg Phe Pro Gly Asp Ser Arg Asp<br>                660                      665                      670 | | | | 2016 |
| tac tcc acg gag cta agc gtg act gta gca gtg ggt gcc tcc ctc ctc<br>Tyr Ser Thr Glu Leu Ser Val Thr Val Ala Val Gly Ala Ser Leu Leu<br>            675                      680                      685 | | | | 2064 |
| ttc ctc aac atc ctt gcc ttt gcc gcc ctc tac tac aag cgg gac cgg<br>Phe Leu Asn Ile Leu Ala Phe Ala Ala Leu Tyr Tyr Lys Arg Asp Arg<br>        690                      695                      700 | | | | 2112 |
| cgc cag gag ctg cgg tgc agg cgg ctt agc cca cca gga ggc tca ggc<br>Arg Gln Glu Leu Arg Cys Arg Arg Leu Ser Pro Pro Gly Gly Ser Gly<br>705                      710                      715                      720 | | | | 2160 |
| tca ggt gtg cct ggt ggg ggc ccc ttg ctt ccc act gct ggc cgt gag<br>Ser Gly Val Pro Gly Gly Gly Pro Leu Leu Pro Thr Ala Gly Arg Glu<br>                      725                      730                      735 | | | | 2208 |
| cta ccc cct gag gag gag ctg gta tcg ctg cag ctg aag cgg ggt ggt<br>Leu Pro Pro Glu Glu Glu Leu Val Ser Leu Gln Leu Lys Arg Gly Gly<br>                740                      745                      750 | | | | 2256 |
| ggc gtt ggg gcg gac cct gct gag gcc ctg cgc cct gcc tgt cca ccc<br>Gly Val Gly Ala Asp Pro Ala Glu Ala Leu Arg Pro Ala Cys Pro Pro<br>            755                      760                      765 | | | | 2304 |
| gac tat acc ctg gcc ttg cgc cgg gca ccg gac gat gtg cct ctc ttg<br>Asp Tyr Thr Leu Ala Leu Arg Arg Ala Pro Asp Asp Val Pro Leu Leu<br>        770                      775                      780 | | | | 2352 |
| gcc ccg ggg gcc ctg acc ctg ctg ccc agt ggc ctg ggg ccc ccg ccc | | | | 2400 |

```
Ala Pro Gly Ala Leu Thr Leu Leu Pro Ser Gly Leu Gly Pro Pro Pro
785                 790                 795                 800 cca ccc cca cct cct tct ctc cat ccc ttt ggg ccc ttc cca cca cca      2448
Pro Pro Pro Pro Pro Ser Leu His Pro Phe Gly Pro Phe Pro Pro Pro
                        805                 810                 815 ccc cct act gct acc agc cac aac aac acg cta ccc cat ccc cac tcc      2496
Pro Pro Thr Ala Thr Ser His Asn Asn Thr Leu Pro His Pro His Ser
                820                 825                 830 acc act cgg gta                                                      2508
Thr Thr Arg Val
            835

<210> SEQ ID NO 6
<211> LENGTH: 836
<212> TYPE: PRT
<213> ORGANISM: Rattus norvegicus

<400> SEQUENCE: 6

Met Trp Leu Leu Ala Leu Cys Leu Val Gly Leu Ala Gly Ala Gln Arg
1               5                   10                  15

Gly Gly Gly Gly Pro Gly Gly Ala Pro Gly Gly Pro Gly Leu Gly
            20                  25                  30

Leu Gly Ser Leu Gly Glu Glu Arg Phe Pro Val Val Asn Thr Ala Tyr
            35                  40                  45

Gly Arg Val Arg Gly Val Arg Arg Glu Leu Asn Asn Glu Ile Leu Gly
        50                  55                  60

Pro Val Val Gln Phe Leu Gly Val Pro Tyr Ala Thr Pro Pro Leu Gly
65              70                  75                  80

Ala Arg Arg Phe Gln Pro Pro Glu Ala Pro Ala Ser Trp Pro Gly Val
                85                  90                  95

Arg Asn Ala Thr Thr Leu Pro Pro Ala Cys Pro Gln Asn Leu His Gly
            100                 105                 110

Ala Leu Pro Ala Ile Met Leu Pro Val Trp Phe Thr Asp Asn Leu Glu
        115                 120                 125

Ala Ala Ala Thr Tyr Val Gln Asn Gln Ser Glu Asp Cys Leu Tyr Leu
130                 135                 140

Asn Leu Tyr Val Pro Thr Glu Asp Gly Pro Leu Thr Lys Lys Arg Asp
145                 150                 155                 160

Glu Ala Thr Leu Asn Pro Pro Asp Thr Asp Ile Arg Asp Ser Gly Lys
                165                 170                 175

Lys Pro Val Met Leu Phe Leu His Gly Gly Ser Tyr Met Glu Gly Thr
            180                 185                 190

Gly Asn Met Phe Asp Gly Ser Val Leu Ala Ala Tyr Gly Asn Val Ile
        195                 200                 205

Val Ala Thr Leu Asn Tyr Arg Leu Gly Val Leu Gly Phe Leu Ser Thr
210                 215                 220

Gly Asp Gln Ala Ala Lys Gly Asn Tyr Gly Leu Leu Asp Gln Ile Gln
225                 230                 235                 240

Ala Leu Arg Trp Leu Ser Glu Asn Ile Ala His Phe Gly Gly Asp Pro
                245                 250                 255

Glu Arg Ile Thr Ile Phe Gly Ser Gly Ala Gly Ala Ser Cys Val Asn
            260                 265                 270

Leu Leu Ile Leu Ser His His Ser Glu Gly Leu Phe Gln Lys Ala Ile
        275                 280                 285

Ala Gln Ser Gly Thr Ala Ile Ser Ser Trp Ser Val Asn Tyr Gln Pro
290                 295                 300
```

```
Leu Lys Tyr Thr Arg Leu Leu Ala Ala Lys Val Gly Cys Asp Arg Glu
305                 310                 315                 320

Asp Ser Thr Glu Ala Val Glu Cys Leu Arg Arg Lys Ser Ser Arg Glu
                325                 330                 335

Leu Val Asp Gln Asp Val Gln Pro Ala Arg Tyr His Ile Ala Phe Gly
            340                 345                 350

Pro Val Val Asp Gly Asp Val Val Pro Asp Pro Glu Ile Leu Met
            355                 360                 365

Gln Gln Gly Glu Phe Leu Asn Tyr Asp Met Leu Ile Gly Val Asn Gln
370                 375                 380

Gly Glu Gly Leu Lys Phe Val Glu Asp Ser Ala Glu Ser Glu Asp Gly
385                 390                 395                 400

Val Ser Ala Ser Ala Phe Asp Phe Thr Val Ser Asn Phe Val Asp Asn
                405                 410                 415

Leu Tyr Gly Tyr Pro Glu Gly Lys Asp Val Leu Arg Glu Thr Ile Lys
            420                 425                 430

Phe Met Tyr Thr Asp Trp Ala Asp Arg Asp Asn Gly Glu Met Arg Arg
                435                 440                 445

Lys Thr Leu Leu Ala Leu Phe Thr Asp His Gln Trp Val Ala Pro Ala
450                 455                 460

Val Ala Thr Ala Lys Leu His Ala Asp Tyr Gln Ser Pro Val Tyr Phe
465                 470                 475                 480

Tyr Thr Phe Tyr His His Cys Gln Ala Glu Gly Arg Pro Glu Trp Ala
                485                 490                 495

Asp Ala Ala His Gly Asp Glu Leu Pro Tyr Val Phe Gly Val Pro Met
            500                 505                 510

Val Gly Ala Thr Asp Leu Phe Pro Cys Asn Phe Ser Lys Asn Asp Val
            515                 520                 525

Met Leu Ser Ala Val Val Met Thr Tyr Trp Thr Asn Phe Ala Lys Thr
530                 535                 540

Gly Asp Pro Asn Gln Pro Val Pro Gln Asp Thr Lys Phe Ile His Thr
545                 550                 555                 560

Lys Pro Asn Arg Phe Glu Glu Val Val Trp Ser Lys Phe Asn Ser Lys
                565                 570                 575

Glu Lys Gln Tyr Leu His Ile Gly Leu Lys Pro Arg Val Arg Asp Asn
            580                 585                 590

Tyr Arg Ala Asn Lys Val Ala Phe Trp Leu Glu Leu Val Pro His Leu
            595                 600                 605

His Asn Leu His Thr Glu Leu Phe Thr Thr Thr Arg Leu Pro Pro
610                 615                 620

Tyr Ala Thr Arg Trp Pro Pro Arg Thr Pro Gly Pro Gly Thr Ser Gly
625                 630                 635                 640

Thr Arg Arg Pro Pro Pro Ala Thr Leu Pro Pro Glu Ser Asp Ile
                645                 650                 655

Asp Leu Gly Pro Arg Ala Tyr Asp Arg Phe Pro Gly Asp Ser Arg Asp
                660                 665                 670

Tyr Ser Thr Glu Leu Ser Val Thr Val Ala Val Gly Ala Ser Leu Leu
            675                 680                 685

Phe Leu Asn Ile Leu Ala Phe Ala Ala Leu Tyr Tyr Lys Arg Asp Arg
690                 695                 700

Arg Gln Glu Leu Arg Cys Arg Arg Leu Ser Pro Pro Gly Gly Ser Gly
705                 710                 715                 720
```

```
Ser Gly Val Pro Gly Gly Pro Leu Leu Pro Thr Ala Gly Arg Glu
            725             730             735

Leu Pro Pro Glu Glu Leu Val Ser Leu Gln Leu Lys Arg Gly Gly
        740             745             750

Gly Val Gly Ala Asp Pro Ala Glu Ala Leu Arg Pro Ala Cys Pro Pro
    755             760             765

Asp Tyr Thr Leu Ala Leu Arg Arg Ala Pro Asp Val Pro Leu Leu
    770             775             780

Ala Pro Gly Ala Leu Thr Leu Leu Pro Ser Gly Leu Gly Pro Pro Pro
785             790             795             800

Pro Pro Pro Pro Ser Leu His Pro Phe Gly Pro Phe Pro Pro Pro
            805             810             815

Pro Pro Thr Ala Thr Ser His Asn Asn Thr Leu Pro His Pro His Ser
            820             825             830

Thr Thr Arg Val
        835

<210> SEQ ID NO 7
<211> LENGTH: 2532
<212> TYPE: DNA
<213> ORGANISM: Artificial Sequence
<220> FEATURE:
<223> OTHER INFORMATION: Flag tag + mouse neuroligin2
<220> FEATURE:
<221> NAME/KEY: CDS
<222> LOCATION: (1)..(2532)
<220> FEATURE:
<221> NAME/KEY: misc_feature
<222> LOCATION: (1)..(27)
<223> OTHER INFORMATION: Flag tag
<220> FEATURE:
<221> NAME/KEY: misc_feature
<222> LOCATION: (28)..(2532)
<223> OTHER INFORMATION: mouse neuroligin2

<400> SEQUENCE: 7 atg gat tac aag gac gac gat gac aag tgg ctc ctg gcg ttg tgt ctg      48
Met Asp Tyr Lys Asp Asp Asp Asp Lys Trp Leu Leu Ala Leu Cys Leu
1               5                   10                  15 gtg ggg ctg gct ggg gct caa cgg gga gga ggg ggt ccc ggc ggc ggc      96
Val Gly Leu Ala Gly Ala Gln Arg Gly Gly Gly Gly Pro Gly Gly Gly
            20                  25                  30 gcc ccg ggc ggc cca ggc ctg ggc ctc ggc agc ctc ggg gag gag cgc     144
Ala Pro Gly Gly Pro Gly Leu Gly Leu Gly Ser Leu Gly Glu Glu Arg
        35                  40                  45 ttc ccc gtg gtg aac aca gcc tac ggg cga gtg cgc ggt gtg cgg cgc     192
Phe Pro Val Val Asn Thr Ala Tyr Gly Arg Val Arg Gly Val Arg Arg
    50                  55                  60 gag ctc aac aac gag atc ctg ggc ccg gtc gtg cag ttc ttg ggc gtg     240
Glu Leu Asn Asn Glu Ile Leu Gly Pro Val Val Gln Phe Leu Gly Val
65                  70                  75                  80 ccc tac gcc acg ccg ccc ttg ggc gcc cgc cgc ttc cag ccg cct gag     288
Pro Tyr Ala Thr Pro Pro Leu Gly Ala Arg Arg Phe Gln Pro Pro Glu
                85                  90                  95 gca cct gcc tcg tgg ccc ggc gtg cgc aac gcc acc acc ctg ccg ccc     336
Ala Pro Ala Ser Trp Pro Gly Val Arg Asn Ala Thr Thr Leu Pro Pro
            100                 105                 110 gcc tgc ccg cag aac ctg cac ggg gcc ctg ccg gcc atc atg ctg cct     384
Ala Cys Pro Gln Asn Leu His Gly Ala Leu Pro Ala Ile Met Leu Pro
        115                 120                 125 gtg tgg ttc acc gac aac ttg gag gcg gcc gcc acc tac gtg cag aac     432
Val Trp Phe Thr Asp Asn Leu Glu Ala Ala Ala Thr Tyr Val Gln Asn
```

-continued

```
                130                 135                 140
cag agc gag gac tgc ctg tac ctc aac ctc tac gtg ccc act gag gac      480
Gln Ser Glu Asp Cys Leu Tyr Leu Asn Leu Tyr Val Pro Thr Glu Asp
145                 150                 155                 160 ggt ccg ctc aca aaa aaa cgt gac gag gcg acg ctc aat ccg cca gac      528
Gly Pro Leu Thr Lys Lys Arg Asp Glu Ala Thr Leu Asn Pro Pro Asp
                165                 170                 175 aca gat atc cgg gac tct ggg aag aaa ccg gtc atg ctg ttt cta cac      576
Thr Asp Ile Arg Asp Ser Gly Lys Lys Pro Val Met Leu Phe Leu His
            180                 185                 190 ggc ggc tcc tac atg gaa ggc acc ggg aac atg ttt gac ggc tca gtc      624
Gly Gly Ser Tyr Met Glu Gly Thr Gly Asn Met Phe Asp Gly Ser Val
        195                 200                 205 ctg gct gcc tat ggc aat gtc atc gta gtc aca ctc aac tac cgt ctt      672
Leu Ala Ala Tyr Gly Asn Val Ile Val Val Thr Leu Asn Tyr Arg Leu
    210                 215                 220 ggg gtg ctc ggt ttt ctc agc act ggt gac cag gct gca aaa ggc aac      720
Gly Val Leu Gly Phe Leu Ser Thr Gly Asp Gln Ala Ala Lys Gly Asn
225                 230                 235                 240 tat ggg ctc ctg gac cag atc cag gcc ctg cgc tgg ctc agt gaa aac      768
Tyr Gly Leu Leu Asp Gln Ile Gln Ala Leu Arg Trp Leu Ser Glu Asn
                245                 250                 255 att gcc cac ttt gga ggt gac cct gaa cgc atc act atc ttt ggg tct      816
Ile Ala His Phe Gly Gly Asp Pro Glu Arg Ile Thr Ile Phe Gly Ser
            260                 265                 270 ggt gca ggg gcc tcc tgt gtc aac ttg ctg atc ctt tcc cac cac tca      864
Gly Ala Gly Ala Ser Cys Val Asn Leu Leu Ile Leu Ser His His Ser
        275                 280                 285 gaa gga ctg ttc cag aag gcc att gct caa agt ggt act gcc att tcc      912
Glu Gly Leu Phe Gln Lys Ala Ile Ala Gln Ser Gly Thr Ala Ile Ser
    290                 295                 300 agc tgg tct gtc aac tac cag ccg ctc aag tac acg cgg ctg ctg gcg      960
Ser Trp Ser Val Asn Tyr Gln Pro Leu Lys Tyr Thr Arg Leu Leu Ala
305                 310                 315                 320 gcc aaa gtg ggc tgt gac cga gaa gac agc act gaa gct gtg gag tgt     1008
Ala Lys Val Gly Cys Asp Arg Glu Asp Ser Thr Glu Ala Val Glu Cys
                325                 330                 335 ctg cgc cgg aag tct tcc cgg gag cta gtg gac cag gat gta cag cct     1056
Leu Arg Arg Lys Ser Ser Arg Glu Leu Val Asp Gln Asp Val Gln Pro
            340                 345                 350 gcc cgc tac cac att gcc ttt ggg cct gtg gtg gac ggc gac gta gtc     1104
Ala Arg Tyr His Ile Ala Phe Gly Pro Val Val Asp Gly Asp Val Val
        355                 360                 365 cct gat gac ccc gag atc ctc atg caa cag ggg gaa ttc ctc aac tac     1152
Pro Asp Asp Pro Glu Ile Leu Met Gln Gln Gly Glu Phe Leu Asn Tyr
    370                 375                 380 gac atg ctc att ggt gtc aac cag gga gag ggt ctc aag ttc gtg gag     1200
Asp Met Leu Ile Gly Val Asn Gln Gly Glu Gly Leu Lys Phe Val Glu
385                 390                 395                 400 gac tct gca gag agt gag gac ggt gtg tct gcc agc gcc ttt gac ttc     1248
Asp Ser Ala Glu Ser Glu Asp Gly Val Ser Ala Ser Ala Phe Asp Phe
                405                 410                 415 acc gtc tcc aac ttt gtg gac aac ttg tac ggg tac cca gaa ggc aag     1296
Thr Val Ser Asn Phe Val Asp Asn Leu Tyr Gly Tyr Pro Glu Gly Lys
            420                 425                 430 gac gtg ctt cga gag acc atc aag ttc atg tac acg gac tgg gct gac     1344
Asp Val Leu Arg Glu Thr Ile Lys Phe Met Tyr Thr Asp Trp Ala Asp
        435                 440                 445 agg gac aat ggc gag atg cgg cgg aag acc ctg ctg gcg ctc ttt acc     1392
```

```
Arg Asp Asn Gly Glu Met Arg Arg Lys Thr Leu Leu Ala Leu Phe Thr
    450                 455                 460 gac cac cag tgg gtc gcc ccg gct gtg gcc acc gcc aag ctg cat gcc    1440
Asp His Gln Trp Val Ala Pro Ala Val Ala Thr Ala Lys Leu His Ala
465                 470                 475                 480 gac tac cag tcc ccc gtc tac ttt tac act ttc tac cac cac tgc cag    1488
Asp Tyr Gln Ser Pro Val Tyr Phe Tyr Thr Phe Tyr His His Cys Gln
                485                 490                 495 gca gag ggc cgg cca gag tgg gca gac gca gcg cac ggg gac gag ctg    1536
Ala Glu Gly Arg Pro Glu Trp Ala Asp Ala Ala His Gly Asp Glu Leu
        500                 505                 510 ccc tac gtc ttt ggt gtc ccc atg gtg ggc gcc act gac ctc ttc ccc    1584
Pro Tyr Val Phe Gly Val Pro Met Val Gly Ala Thr Asp Leu Phe Pro
            515                 520                 525 tgc aac ttc tcc aag aac gat gtc atg ctc agc gca gta gtc atg acc    1632
Cys Asn Phe Ser Lys Asn Asp Val Met Leu Ser Ala Val Val Met Thr
530                 535                 540 tat tgg acc aac ttc gcc aag act ggt gac ccc aac cag cct gtg cca    1680
Tyr Trp Thr Asn Phe Ala Lys Thr Gly Asp Pro Asn Gln Pro Val Pro
545                 550                 555                 560 cag gac acc aag ttc atc cac acc aag ccc aac cgc ttt gaa gag gta    1728
Gln Asp Thr Lys Phe Ile His Thr Lys Pro Asn Arg Phe Glu Glu Val
                565                 570                 575 gtg tgg agc aag ttc aac agc aag gaa aag cag tat ctg cac ata ggc    1776
Val Trp Ser Lys Phe Asn Ser Lys Glu Lys Gln Tyr Leu His Ile Gly
        580                 585                 590 ttg aaa cca cgc gtg cgc gac aac tac cgt gcc aac aag gtg gcc ttc    1824
Leu Lys Pro Arg Val Arg Asp Asn Tyr Arg Ala Asn Lys Val Ala Phe
            595                 600                 605 tgg ctg gag ctc gtg ccc cac ctg cac aac ctg cac aca gag ctc ttc    1872
Trp Leu Glu Leu Val Pro His Leu His Asn Leu His Thr Glu Leu Phe
610                 615                 620 acc acc acc act cgc ctg cct ccc tat gcc aca cgc tgg cca cct cgc    1920
Thr Thr Thr Thr Arg Leu Pro Pro Tyr Ala Thr Arg Trp Pro Pro Arg
625                 630                 635                 640 aca cct ggt cct ggc act tcc ggc aca cgc cgt cct ccc cca cct gcc    1968
Thr Pro Gly Pro Gly Thr Ser Gly Thr Arg Arg Pro Pro Pro Pro Ala
                645                 650                 655 act ctg cca cct gag tct gat att gac cta ggc cca agg gcc tat gac    2016
Thr Leu Pro Pro Glu Ser Asp Ile Asp Leu Gly Pro Arg Ala Tyr Asp
        660                 665                 670 cgc ttc ccc ggt gac tcg agg gac tac tcc acg gag cta agc gtg act    2064
Arg Phe Pro Gly Asp Ser Arg Asp Tyr Ser Thr Glu Leu Ser Val Thr
            675                 680                 685 gtg gca gtg ggt gcc tcc ctc ctc ttc ctc aac atc ctt gcc ttt gcc    2112
Val Ala Val Gly Ala Ser Leu Leu Phe Leu Asn Ile Leu Ala Phe Ala
690                 695                 700 gcc ctc tat tac aag cgg gac cgg cgc cag gag ctg cgg tgc cgg agg    2160
Ala Leu Tyr Tyr Lys Arg Asp Arg Arg Gln Glu Leu Arg Cys Arg Arg
705                 710                 715                 720 ctt agc cca cca gga ggc tca ggc tca ggt gtg cct ggt ggg ggc ccc    2208
Leu Ser Pro Pro Gly Gly Ser Gly Ser Gly Val Pro Gly Gly Gly Pro
                725                 730                 735 ctg ctt ccc act gct ggc cgt gag cta ccc ccg gag gag gag cta gta    2256
Leu Leu Pro Thr Ala Gly Arg Glu Leu Pro Pro Glu Glu Glu Leu Val
        740                 745                 750 tcg ctg cag ctg aag cgg ggt ggt ggt gtt ggg gcg gac cct gct gag    2304
Ser Leu Gln Leu Lys Arg Gly Gly Gly Val Gly Ala Asp Pro Ala Glu
            755                 760                 765
```

```
gcc ctg cgc cct gcc tgt cca ccc gac tat acc ctg gcc ttg cgc cgg    2352
Ala Leu Arg Pro Ala Cys Pro Pro Asp Tyr Thr Leu Ala Leu Arg Arg
770             775                 780 gca ccg gac gat gtg cct ctc ttg gcc ccc ggg gcc cta acc ctg ctg    2400
Ala Pro Asp Asp Val Pro Leu Leu Ala Pro Gly Ala Leu Thr Leu Leu
785             790                 795                 800 cct agt ggc ctg ggg ccc ccg ccc ccg ccc cca ccc cct tct ctc cat    2448
Pro Ser Gly Leu Gly Pro Pro Pro Pro Pro Pro Pro Pro Ser Leu His
            805                 810                 815 ccc ttt ggg ccc ttc cca ccc cca ccc cct act gct acc agc cac aac    2496
Pro Phe Gly Pro Phe Pro Pro Pro Pro Pro Pro Thr Ala Thr Ser His Asn
            820                 825                 830 aac acg cta ccc cat ccc cac tcc acc act cgg gta                    2532
Asn Thr Leu Pro His Pro His Ser Thr Thr Arg Val
            835                 840

<210> SEQ ID NO 8
<211> LENGTH: 844
<212> TYPE: PRT
<213> ORGANISM: Artificial Sequence
<220> FEATURE:
<223> OTHER INFORMATION: Synthetic Construct

<400> SEQUENCE: 8

Met Asp Tyr Lys Asp Asp Asp Lys Trp Leu Leu Ala Leu Cys Leu
1               5                   10                  15

Val Gly Leu Ala Gly Ala Gln Arg Gly Gly Gly Pro Gly Gly Gly
                20                  25                  30

Ala Pro Gly Gly Pro Gly Leu Gly Leu Gly Ser Leu Gly Glu Glu Arg
        35                  40                  45

Phe Pro Val Val Asn Thr Ala Tyr Gly Arg Val Arg Gly Val Arg Arg
50                  55                  60

Glu Leu Asn Asn Glu Ile Leu Gly Pro Val Val Gln Phe Leu Gly Val
65                  70                  75                  80

Pro Tyr Ala Thr Pro Pro Leu Gly Ala Arg Arg Phe Gln Pro Pro Glu
                85                  90                  95

Ala Pro Ala Ser Trp Pro Gly Val Arg Asn Ala Thr Thr Leu Pro Pro
            100                 105                 110

Ala Cys Pro Gln Asn Leu His Gly Ala Leu Pro Ala Ile Met Leu Pro
        115                 120                 125

Val Trp Phe Thr Asp Asn Leu Glu Ala Ala Ala Thr Tyr Val Gln Asn
130                 135                 140

Gln Ser Glu Asp Cys Leu Tyr Leu Asn Leu Tyr Val Pro Thr Glu Asp
145                 150                 155                 160

Gly Pro Leu Thr Lys Lys Arg Asp Glu Ala Thr Leu Asn Pro Pro Asp
                165                 170                 175

Thr Asp Ile Arg Asp Ser Gly Lys Lys Pro Val Met Leu Phe Leu His
            180                 185                 190

Gly Gly Ser Tyr Met Glu Gly Thr Gly Asn Met Phe Asp Gly Ser Val
        195                 200                 205

Leu Ala Ala Tyr Gly Asn Val Ile Val Val Thr Leu Asn Tyr Arg Leu
210                 215                 220

Gly Val Leu Gly Phe Leu Ser Thr Gly Asp Gln Ala Ala Lys Gly Asn
225                 230                 235                 240

Tyr Gly Leu Leu Asp Gln Ile Gln Ala Leu Arg Trp Leu Ser Glu Asn
                245                 250                 255

Ile Ala His Phe Gly Gly Asp Pro Glu Arg Ile Thr Ile Phe Gly Ser
```

```
                260                 265                 270
Gly Ala Gly Ala Ser Cys Val Asn Leu Leu Ile Leu Ser His His Ser
            275                 280                 285

Glu Gly Leu Phe Gln Lys Ala Ile Ala Gln Ser Gly Thr Ala Ile Ser
            290                 295                 300

Ser Trp Ser Val Asn Tyr Gln Pro Leu Lys Tyr Thr Arg Leu Leu Ala
305                 310                 315                 320

Ala Lys Val Gly Cys Asp Arg Glu Asp Ser Thr Glu Ala Val Glu Cys
                325                 330                 335

Leu Arg Arg Lys Ser Ser Arg Glu Leu Val Asp Gln Asp Val Gln Pro
            340                 345                 350

Ala Arg Tyr His Ile Ala Phe Gly Pro Val Val Asp Gly Asp Val Val
            355                 360                 365

Pro Asp Asp Pro Glu Ile Leu Met Gln Gln Gly Glu Phe Leu Asn Tyr
            370                 375                 380

Asp Met Leu Ile Gly Val Asn Gln Gly Glu Gly Leu Lys Phe Val Glu
385                 390                 395                 400

Asp Ser Ala Glu Ser Glu Asp Gly Val Ser Ala Ser Ala Phe Asp Phe
                405                 410                 415

Thr Val Ser Asn Phe Val Asp Asn Leu Tyr Gly Tyr Pro Glu Gly Lys
            420                 425                 430

Asp Val Leu Arg Glu Thr Ile Lys Phe Met Tyr Thr Asp Trp Ala Asp
            435                 440                 445

Arg Asp Asn Gly Glu Met Arg Arg Lys Thr Leu Leu Ala Leu Phe Thr
            450                 455                 460

Asp His Gln Trp Val Ala Pro Ala Val Ala Thr Ala Lys Leu His Ala
465                 470                 475                 480

Asp Tyr Gln Ser Pro Val Tyr Phe Tyr Thr Phe Tyr His His Cys Gln
                485                 490                 495

Ala Glu Gly Arg Pro Glu Trp Ala Asp Ala Ala His Gly Asp Glu Leu
            500                 505                 510

Pro Tyr Val Phe Gly Val Pro Met Val Gly Ala Thr Asp Leu Phe Pro
            515                 520                 525

Cys Asn Phe Ser Lys Asn Asp Val Met Leu Ser Ala Val Val Met Thr
            530                 535                 540

Tyr Trp Thr Asn Phe Ala Lys Thr Gly Asp Pro Asn Gln Pro Val Pro
545                 550                 555                 560

Gln Asp Thr Lys Phe Ile His Thr Lys Pro Asn Arg Phe Glu Glu Val
                565                 570                 575

Val Trp Ser Lys Phe Asn Ser Lys Glu Lys Gln Tyr Leu His Ile Gly
            580                 585                 590

Leu Lys Pro Arg Val Arg Asp Asn Tyr Arg Ala Asn Lys Val Ala Phe
            595                 600                 605

Trp Leu Glu Leu Val Pro His Leu His Asn Leu His Thr Glu Leu Phe
            610                 615                 620

Thr Thr Thr Thr Arg Leu Pro Pro Tyr Ala Thr Arg Trp Pro Pro Arg
625                 630                 635                 640

Thr Pro Gly Pro Gly Thr Ser Gly Thr Arg Arg Pro Pro Pro Ala
                645                 650                 655

Thr Leu Pro Pro Glu Ser Asp Ile Asp Leu Gly Pro Arg Ala Tyr Asp
            660                 665                 670

Arg Phe Pro Gly Asp Ser Arg Asp Tyr Ser Thr Glu Leu Ser Val Thr
            675                 680                 685
```

```
Val Ala Val Gly Ala Ser Leu Leu Phe Leu Asn Ile Leu Ala Phe Ala
        690                 695                 700

Ala Leu Tyr Tyr Lys Arg Asp Arg Arg Gln Glu Leu Arg Cys Arg Arg
705                 710                 715                 720

Leu Ser Pro Pro Gly Ser Gly Ser Gly Val Pro Gly Gly Gly Pro
                725                 730                 735

Leu Leu Pro Thr Ala Gly Arg Glu Leu Pro Glu Glu Leu Val
                740                 745                 750

Ser Leu Gln Leu Lys Arg Gly Gly Val Gly Ala Asp Pro Ala Glu
            755                 760                 765

Ala Leu Arg Pro Ala Cys Pro Pro Asp Tyr Thr Leu Ala Leu Arg Arg
        770                 775                 780

Ala Pro Asp Asp Val Pro Leu Leu Ala Pro Gly Ala Leu Thr Leu Leu
785                 790                 795                 800

Pro Ser Gly Leu Gly Pro Pro Pro Pro Pro Pro Ser Leu His
                805                 810                 815

Pro Phe Gly Pro Phe Pro Pro Pro Pro Thr Ala Thr Ser His Asn
                820                 825                 830

Asn Thr Leu Pro His Pro His Ser Thr Thr Arg Val
            835                 840
```

<210> SEQ ID NO 9
<211> LENGTH: 736
<212> TYPE: PRT
<213> ORGANISM: Artificial Sequence
<220> FEATURE:
<223> OTHER INFORMATION: Synthetic Construct

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205
```

```
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
            325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
            405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Phe Leu Asn Arg
        435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
            485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
            515                 520                 525
Asp Asp Glu Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
            565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
```

```
Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
        645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 10
<211> LENGTH: 735
<212> TYPE: PRT
<213> ORGANISM: Artificial Sequence
<220> FEATURE:
<223> OTHER INFORMATION: Synthetic Construct

<400> SEQUENCE: 10

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255
```

-continued

```
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
        290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Phe Leu Ser Arg Thr
            435                 440                 445
Asn Thr Pro Ser Gly Thr Thr Thr Gln Ser Arg Leu Gln Phe Ser Gln
        450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
        530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
        610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
```

```
                   675                 680                 685
Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 11
<211> LENGTH: 736
<212> TYPE: PRT
<213> ORGANISM: Artificial Sequence
<220> FEATURE:
<223> OTHER INFORMATION: Synthetic Construct

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
```

-continued

```
            305                 310                 315                 320

Gln Val Lys Glu Val Thr Asp Asn Asn Gly Val Lys Thr Ile Ala Asn
                        325                 330                 335

Asn Leu Thr Ser Thr Val Gln Val Phe Thr Asp Ser Asp Tyr Gln Leu
                        340                 345                 350

Pro Tyr Val Leu Gly Ser Ala His Glu Gly Cys Leu Pro Pro Phe Pro
                        355                 360                 365

Ala Asp Val Phe Met Ile Pro Gln Tyr Gly Tyr Leu Thr Leu Asn Asp
                        370                 375                 380

Gly Ser Gln Ala Val Gly Arg Ser Ser Phe Tyr Cys Leu Glu Tyr Phe
        385                 390                 395                 400

Pro Ser Gln Met Leu Arg Thr Gly Asn Asn Phe Gln Phe Ser Tyr Glu
                        405                 410                 415

Phe Glu Asn Val Pro Phe His Ser Ser Tyr Ala His Ser Gln Ser Leu
                        420                 425                 430

Asp Arg Leu Met Asn Pro Leu Ile Asp Gln Tyr Leu Tyr Phe Leu Ser
                        435                 440                 445

Lys Thr Ile Asn Gly Ser Gly Gln Asn Gln Gln Thr Leu Lys Phe Ser
                        450                 455                 460

Val Ala Gly Pro Ser Asn Met Ala Val Gln Gly Arg Asn Tyr Ile Pro
        465                 470                 475                 480

Gly Pro Ser Tyr Arg Gln Gln Arg Val Ser Thr Thr Val Thr Gln Asn
                        485                 490                 495

Asn Asn Ser Glu Phe Ala Trp Pro Gly Ala Ser Ser Trp Ala Leu Asn
                        500                 505                 510

Gly Arg Asn Ser Leu Met Asn Pro Gly Pro Ala Met Ala Ser His Lys
                        515                 520                 525

Glu Gly Glu Asp Arg Phe Phe Pro Leu Ser Gly Ser Leu Ile Phe Gly
                        530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                        565                 570                 575

Tyr Gly Gln Val Ala Thr Asn His Gln Ser Ala Gln Ala Gln Ala Gln
                        580                 585                 590

Thr Gly Trp Val Gln Asn Gln Gly Ile Leu Pro Gly Met Val Trp Gln
                        595                 600                 605

Asp Arg Asp Val Tyr Leu Gln Gly Pro Ile Trp Ala Lys Ile Pro His
                        610                 615                 620

Thr Asp Gly Asn Phe His Pro Ser Pro Leu Met Gly Gly Phe Gly Met
        625                 630                 635                 640

Lys His Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                        660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Ile Gln Tyr Thr Ser Asn
        690                 695                 700
```

-continued

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

ADENO-ASSOCIATED VIRUS VIRIONS FOR TREATMENT OF EPILEPSY

Sequence Listing Submission via EFS-Web

A computer readable text file, entitled "SequenceListing.txt," created on or about Jul. 10, 2018 with a file size of about 96 kb contains the sequence listing for this application and is hereby incorporated by reference in its entirety.

TECHNICAL FIELD

The present invention relates to genetically recombinant adeno-associated virus (rAAV) virions for neural diseases. More specifically, the present invention relates to rAAV for treatment of neuropsychiatric diseases such as epilepsy, schizophrenia, autism spectrum disorder, mental retardation, anxiety, manic-depressive psychosis, migraine, phobic and compulsive symptoms, drug addiction, Angelman syndrome, dyskinesia, dystonia, Alzheimer's disease, and developmental disorders (attention deficit hyperactivity disorder and Asperger's syndrome).

BACKGROUND ART

Epilepsy is classified into partial convulsions that are seizures generated partially in body parts as a result of occurrence of the abnormal excitation of neurons in the brain at relatively limited sites, and generalized seizures (e.g., tonic-clonic seizures) that are generalized convulsions generated because the abnormally excited neurons in the brain affect the cortex entirely. A generalized seizure causes the loss of consciousness, and is a disease that causes no convulsion, but may cause impaired consciousness alone or abnormal psychiatric symptoms (e.g, psychomotor seizures). Current general therapeutic approaches are mainly pharmacotherapies using antiepileptic drugs (e.g., phenytoin, carbamazepine, and valproic acid). Surgical treatment is also performed for intractable epilepsy cases.

About 30% of epilepsy cases is accounted for by intractable diseases, the seizures of which are not suppressed by drug treatment. In the case of inner temporal lobe epilepsy, surgical treatment such as temporal lobectomy may be effective. However, the excision of bilateral hippocampi causes a decrease in memory retention, so that if seizure foci are located in bilateral hippocampi, such a case is not a candidate for surgery. Moreover, the number of patients with intractable epilepsy such as childhood epileptic encephalopathy (e.g., West syndrome) having unknown seizure foci is estimated to be about 100,000 in Japan, and no curable therapy exists for such patients.

To treat such intractable epilepsy, a method for treating each disease by a gene therapy targeting nerve cells has also been examined. As a means (vector) for delivering a therapeutic gene to nerve cells, a means of using a recombinant adeno-associated virus (rAAV) is known in the art. Examples of such rAAV include those disclosed in International Publications WO2012/057363, WO2008/124724, WO2003/093479, and the like.

Means for adjusting neural activity targeting synapse-associated proteins have been studied. For example, the document of Kohl, C et al. (Non Patent Literature 1) discloses that the direct administration of an rAAV vector expressing neuroligin 2 (NLGN2) that is a synapse localized protein of nerve cells to hippocampi to overexpress NLGN2, results in altered social behavior and inhibitory synaptic transmission, but does not describe any specific treatment of the disease. The document of Moe et al. (Non Patent Literature 2) discloses that epilepsy symptoms are alleviated by treatment of epilepsy using an rAAV vector expressing neuropeptide Y. Moreover, the document of Fang et al. (Non Patent Literature 3) discloses that epilepsy symptoms are alleviated as a result of direct administration of an rAAV vector expressing the antisense of neuroligin 1 (NLGN1) that is a synapse localized protein of nerve cells to hippocampi.

PRIOR ART DOCUMENTS

Patent Literatures

Patent Literature 1: WO 2012/057363
Patent Literature 2: WO 2008/124724
Patent Literature 3: WO 2003/093479

Non Patent Literatures

Non Patent Literature 1: Kohl, C. et al., PLOS ONE, 2013 February, vol. 8, e56871
Non Patent Literature 2: Moe', F. M. et al., JASPER'S BASIC MECHANISMS OF THE EPILEPSY, 2012,
Non Patent Literature 3: Kullmann, D. M. et al., Nature Reviews Neurology, 2014, vol. 10, page 300-304
Non Patent Literature 4: Fang et al., Mol. Neurobiol. 2014 Nov. 27 [Epub]

SUMMARY OF INVENTION

Technical Problem

A novel medicine for treating epilepsy by gene transfer is required. Furthermore, such a medicine is desired to be advantageous in actual medication such that it has fewer side effects, and can be more simply administered, for example.

Solution to Problem

As a result of intensive studies to establish a gene therapy for epilepsy, the inventors of the present application have discovered that through preparation of a recombinant adeno-associated virus vector comprising a polynucleotide encoding neuroligin 2 that is a protein for improving the excitation-inhibiting capability of inhibitory synapses, and administration of the vector to a living subject, epilepsy symptoms are improved, and thus have completed the invention of the present application.

Specifically, the present application provides a recombinant adeno-associated virus (rAAV) vector as described below for treatment of the following nerve cell-related diseases such as epilepsy, and a pharmaceutical composition comprising the vector, for example.

{1} A recombinant adeno-associated virus vector, comprising a polynucleotide encoding a protein for improving an excitation-inhibiting function of inhibitory synapses in a living subject, which is used for treatment of a disease selected from the group consisting of epilepsy, schizophrenia, autism spectrum disorder, mental retardation, anxiety, manic-depressive psychosis, migraine, phobic and compulsive symptoms, drug addiction, Angelman syndrome, dyskinesia, dystonia, Alzheimer's disease, and developmental disorders (attention deficit hyperactivity disorder and Asperger's syndrome).

{2} The recombinant adeno-associated virus vector according to {1}, wherein the polynucleotide comprises a nucleotide sequence encoding a neuroligin 2 protein which comprises the amino acid sequence of SEQ ID NO: 2, 4 or 6, or an amino acid sequence having about 90% or more identity with said amino acid sequence and binding to neurexin.

{3} The recombinant adeno-associated virus vector according to {1} or {2}, wherein the disease is epilepsy.

{4} The adeno-associated virus recombinant vector according to any one of {1} to {3}, wherein the recombinant adeno-associated virus vector comprises:
a protein having a variant amino acid sequence in which tyrosine at position 445 in the amino acid sequence of the wild-type AAV1 capsid protein is substituted with phenylalanine;
a protein having a variant amino acid sequence in which tyrosine at position 445 in the amino acid sequence of the wild-type AAV2 capsid protein is substituted with phenylalanine; or
a protein having a variant amino acid sequence in which tyrosine at position 446 in the amino acid sequence of the wild-type AAV9 capsid protein is substituted with phenylalanine.

{5} The recombinant adeno-associated virus vector according to any one of {1} to {4}, wherein the above polynucleotide comprises a promoter sequence selected from the group consisting of a synapsin I promoter sequence, a myelin basic protein promoter sequence, a neuron specific enolase promoter sequence, a calcium/calmodulin-dependent protein kinase II (CMKII) promoter sequence, a tubulin αI promoter sequence, a platelet-derived growth factor β chain promoter sequence, a glial fibrillary acidic protein (GFAP) promoter sequence, a L7 promoter (cerebellar Purkinje cell specific promoter) sequence, a glial fibrillary acidic protein (hGfa2) promoter sequence, and a glutamate receptor delta 2 promoter (cerebellar Purkinje cell specific promoter) sequence, and a glutamic acid decarboxylase (GAD65/GAD67) promoter sequence.

{6} The recombinant adeno-associated virus vector according to any one of {1} to {5}, wherein the above polynucleotide comprises an inverted terminal repeat (ITR) selected from the group consisting of AAV1, AAV2, AAV3, AAV4, AAV8, and AAV9.

{7} The recombinant adeno-associated virus vector according to any one of {1} to {6}, wherein the above polynucleotide further comprises a polynucleotide for inhibiting the excitation of excitatory synapses.

{8} A pharmaceutical composition, comprising the recombinant adeno-associated virus vector according to any one of {1} to {7}.

{9} The pharmaceutical composition according to {8}, which is administered intracerebrally.

{10} The pharmaceutical composition according to {8}, which is administered intrathecally.

{11} The pharmaceutical composition according to {8}, which is administered peripherally.

{12} The pharmaceutical composition according to any one of {8} to {11}, which is used in combination with a chemotherapeutic agent for a neuropsychiatric disease.

{13} A method for treatment of a disease selected from the group consisting of epilepsy, schizophrenia, autism spectrum disorder, mental retardation, anxiety, manic-depressive psychosis, migraine, phobic and compulsive symptoms, drug addiction, Angelman syndrome, dyskinesia, dystonia, Alzheimer's disease, and developmental disorders (attention deficit hyperactivity disorder and Asperger's syndrome), comprising administering to the living subject a recombinant adeno-associated virus vector that comprises a polynucleotide having a nucleotide sequence encoding a protein for improving the excitation-inhibiting function of inhibitory synapses in a living subject.

{14} The treatment method according to {13}, which is combined with a chemotherapy.

Advantageous Effects of Invention

Enhancement of the functions of a synaptic inhibitory system by a gene therapy according to the invention of the present application is useful as a method for treatment of epilepsy. The composition of the invention of the present application can be expected to be effective for even patients with intractable epilepsy having unspecified seizure foci, such as childhood epileptic encephalopathy (e.g., West syndrome).

BRIEF DESCRIPTION OF DRAWINGS

FIG. 1a shows the result of confirming the expression of the recombinant neuroligin 2 protein in a mouse to which vascular-administration-type rAAV was administered by the FLAG antibody staining of tissue sections. FIG. 1b shows the result of detecting the expression of the recombinant neuroligin 2 in a mouse to which a control was administered.

FIG. 2 shows the results of measuring epileptic seizure frequencies of mice subjected to 3 types of intracardiac administration (intracardiac administration of vascular-administration-type rAAV expressing NLGN2, vascular-administration-type rAAV expressing GFP protein, and physiological saline) at ages in weeks plotted on the horizontal axis.

FIG. 3 shows the results of seizure duration of mice subjected to the above 3 types of intracardiac administration.

FIG. 4 shows the results of seizure intensity of mice subjected to the above 3 types of intracardiac administration.

FIG. 5 shows the results of aggregating the results of seizure duration×seizure intensity in FIG. 3 and FIG. 4.

FIG. 6 shows the results of thresholds when mice subjected to the above 3 types of administration were subjected to electric stimulation at each age in weeks.

FIG. 7a shows the results of measuring the seizure frequencies of epilepsy of mice to which vascular-administration-type rAAV expressing NLGN2, vascular-administration-type rAAV expressing GFP protein, and physiological saline were topically administered to hippocampi at ages in weeks indicated on the horizontal axis (FIG. 7a), as well as the results of the same of mice to which vascular-administration-type rAAV expressing NLGN2, and vascular-administration-type rAAV expressing GFP protein were intracardially administered at ages in weeks plotted on the horizontal axis (FIG. 7b).

FIG. 8 shows the results of measuring seizure duration of mice in FIG. 7.

FIG. 9 shows the results of measuring seizure intensity of mice in FIG. 7.

FIG. 10 shows the aggregated results of seizure duration× seizure intensity of mice in FIG. 7.

FIG. 11 shows thresholds of electric stimulation measured at each age in weeks of mice in FIG. 7.

DESCRIPTION OF EMBODIMENTS

In this application, a recombinant adeno-associated virus vector is provided for treatment of a disease selected from the group consisting of epilepsy, schizophrenia, autism spectrum disorder, mental retardation, anxiety, manic-depressive psychosis, migraine, phobic and compulsive symptoms, drug addiction, Angelman syndrome, dyskinesia, dystonia, Alzheimer's disease, developmental disorders (attention deficit hyperactivity disorder, and Asperger's syndrome), which comprises a polynucleotide encoding a protein for improving the excitation-inhibiting function of inhibitory synapses in a living subject.

1. Excitation Control in Excitatory Synapse and Inhibitory Synapse

In this application, the term "synapse(s)" refers to junctional complexes between a synaptic knob formed of each swollen axonal terminal of nerve cells, and its target neuron or myocyte. In a living subject, excitatory synapses for transmitting excitation and inhibitory synapses for inhibiting the excitation transmission are present. Moreover, most synapses are chemical synapses (slow signal transduction) that are mediated by transmission of chemical substances. Another type of synapses includes electric synapses exhibiting quick response in terms of time, but are uncommonly observed in the central nervous system of a mature mammal.

In excitatory synapses, amino acids such as glutamic acid, aspartic acid, cysteic acid, and homocysteic acid function as transmitters, excitatory postsynaptic potential (EPSP) is generated, and then when the electric potential exceeds a threshold, excitation (impulse) transmission is performed. On the other hand, in inhibitory synapses, amino acids such as γ-aminobutyric acid (GABA), glycine, taurine, alanine, cystathionine, and serine function as transmitters, and then inhibitory postsynaptic potential (IPSP) is generated, which is considered to suppress the impulse of postsynaptic neurons or makes the generation thereof difficult. EPSP and IPSP include fast EPSP or fast IPSP exhibiting a rapid time course (the entire time course is within 100 milliseconds) and slow EPSP or slow IPSP exhibiting extremely slow time course lasting for tens of seconds to tens of minutes. Here, in rapid IPSP, GABA associated with a $GABA_A$ receptor ($Cl^-$) channel and glycine associated with a glycine receptor ($Cl^-$) channel are known to act. As slow IPSP transmitters, $GABA_B$ acting through a $GABA_B$ receptor as well as acetylcholine and catecholamine are known to act.

Examples of a protein for improving the excitation-inhibiting function of inhibitory synapses include neuroligin 2 and neurexin involved in synapse stabilization, GABA receptor, glutaminedecarboxylase (GAD) involved in GABA biosynthesis, $Na^+$ channel protein and $Cl^-$ channel protein involved in glycine transport, neuropeptide Y, gephyrin that is a scaffold protein, SLITRK3 that is a transmembrane protein and involved in inhibitory synapse formation, and PTPRD that is receptor-type tyrosine phosphatase binding to SLITRK3. A polynucleotide contained in the vector of the present invention comprises preferably a nucleotide sequence encoding a neuroligin 2 protein (SEQ ID NO: 2, 4 or 6) as a protein for improving the excitation-inhibiting function of inhibitory synapses.

The term "neuroligin (NLGN)" refers to a membrane protein family existing in a postsynaptic membrane, and is generally classified into neuroligins 1 to 4. Each of these neuroligins specifically binds to a cell adhesion molecule neurexin (Neurexin: NRXN) protein of a presynaptic membrane in order to connect a synapse preterminal and a postsynaptic site. Neuroligin 1 is located in excitatory synapses, and is considered to mediate excitatory synaptic transmission. On the other hand, neuroligin 2 is located in inhibitory synapses, and is considered to mediate inhibitory synaptic transmission. Moreover, neuroligin 3 is expressed in both excitatory synapses and inhibitory synapses, heart, pancreas, and the like, and neuroligin 4 is expressed in heart, liver and the like.

Neurexin proteins that are binding partners of neuroligins are generally classified into neurexin 1α to 3α and 1β to 3β. Herein, α neurexins and β neurexins are long-chain proteins and short-chain proteins, respectively, which are generated from the same gene by the action of different promoters. Neuroligin 2 to be used in the invention of the present application functionally binds to neurexin 1α.

A known amino acid sequence can be used as the amino acid sequence of the neuroligin 2 protein to be used in the invention of the present application. Examples of such amino acid sequence include Genbank Accession No. AAM46111 (human), EDL12455 (mouse), and EDM04903 (rat). Examples of such proteins of other animal species that can be used herein include proteins derived from mammals such as monkey, dog, pig, cattle and horse. The amino acid sequences of human, mouse and rat neuroligin 2 proteins are represented by SEQ ID NO: 2, 4 and 6, respectively.

Furthermore, examples of the neuroligin 2 protein to be used in the invention of the present application include a protein that has an amino acid sequence having about 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more identity with the amino acid sequence of SEQ ID NO: 2, 4 or 6, and is capable of binding to a neurexin 1α protein under physiological conditions. The larger numerical values are generally more preferred. In addition, the amino acid sequence of human neuroligin 2 and that of mouse neuroligin 2 share 98% or more identity, and the amino acid sequence of human neuroligin 2 and that of rat neuroligin 2 share 91% or more identity. In the present invention, the phrase "a variant protein functions to a degree equivalent to that of the original protein" (for example, a protein exhibits binding ability equivalent to that of the original protein) means that, for example, the specific activity ranges from about 0.01 to 100, preferably ranges from about 0.5 to 20, and more preferably ranges from about 0.5 to 2, but examples thereof are not limited thereto.

Furthermore, examples of the neuroligin 2 protein to be used in the invention of the present application include a protein comprising the amino acid sequence of SEQ ID NO: 2, 4 or 6 or an amino acid sequence that has the above identity with the amino acid sequence of SEQ ID NO: 2, 4 or 6, in which one or more amino acids are deleted, substituted, inserted and/or added, and is capable of binding to the neurexin 1α protein under physiological conditions. Among the above amino acid deletion, substitution, insertion and addition, two or more types thereof may take place simultaneously. An example of such a protein is a protein comprising an amino acid sequence that is prepared from the amino acid sequence of SEQ ID NO: 2, 4 or 6 by deletion, substitution, insertion and/or addition of, for example, 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or one amino acid residue, and is capable of binding to a neurexin a protein under physiological conditions. The smaller number of the above amino acid residues to be deleted, substituted, inserted and/or added are generally more preferred.

Examples of amino acid residues in the protein (polypeptide) of the present invention, which can be substituted with each other, are as described below. Amino acid residues included in the same group can be substituted with each other.

Group A: leucine, isoleucine, norleucine, valine, norvaline, alanine, 2-aminobutanoic acid, methionine, o-methylserine, t-butylglycine, t-butylalanine, and cyclohexylalanine;

Group B: aspartic acid, glutamic acid, isoaspartic acid, isoglutamic acid, 2-aminoadipic acid, and 2-aminosuberic acid;

Group C: asparagine, and glutamine;

Group D: lysine, arginine, ornithine, 2,4-diaminobutanoic acid, and 2,3-diaminopropionic acid;

Group E: proline, 3-hydroxyproline, and 4-hydroxyproline;

Group F: serine, threonine, and homoserine; and

Group G: phenylalanine, and tyrosine.

A neuroligin protein in which an amino acid residue(s) is substituted can be prepared according to a method known by persons skilled in the art, such as a general genetic engineering technique. Such genetic engineering procedures can be referred to, for example, Molecular Cloning 3rd Edition, J. Sambrook et al., Cold Spring Harbor Lab. Press. 2001, Current Protocols in Molecular Biology, John Wiley & Sons 1987-1997.

Furthermore, examples of a polynucleotide that is preferably used in the invention of the present application include a polynucleotide having the polynucleotide sequence of SEQ ID NO: 1, 3 or 5, in which 1 or more (for example, 1 to 50, 1 to 40, 1 to 30, 1 to 25, 1 to 20, 1 to 15, 1 to 10, 1 to 9 (1 to several), 1 to 8, 1 to 7, 1 to 6, 1 to 5, 1 to 4, 1 to 3, 1 to 2, and 1) nucleotides are deleted, substituted, inserted and/or added, and encoding the protein that comprises the amino acid sequence of SEQ ID NO: 2, 4 or 6, or a protein that comprises an amino acid sequence prepared from the amino acid sequence of SEQ ID NO: 2, 4 or 6 by deletion, substitution, insertion and/or addition of one or more amino acids as described above, and is capable of binding to a neurexin 1α. Among these deletion, substitution, insertion and addition, two or more types thereof may be contained in combination simultaneously. A smaller number of the above nucleotides to be deleted, substituted, inserted and/or added are generally more preferred. Moreover, examples of a preferable polynucleotide in the invention of the present application include a polynucleotide which is hybridizable under stringent hybridization conditions to SEQ ID NO: 7, 9 or 11 or its complementary sequence and encodes the amino acid sequence of SEQ ID NO: 2, 4 or 6, and a polynucleotide encoding a protein which comprises an amino acid sequence prepared from the amino acid sequence of SEQ ID NO: 2, 4 or 6 by deletion, substitution, insertion and/or addition of one or more amino acids as described above, and is capable of binding to a neurexin.

Hybridization can be performed by well-known methods or methods modified therefrom, for example, methods described in Molecular Cloning (3rd Edition, J. Sambrook et al., Cold Spring Harbor Lab. Press. 2001), etc. When commercially-available libraries are used, hybridization may be performed in accordance with the methods described in instructions provided by manufacturers, etc. As used herein, the term "stringent conditions" may be any of low stringent conditions, moderate stringent conditions and high stringent conditions. The term "low stringent conditions" refers to conditions of, for example, 5×SSC, 5×Denhardt's solution, 0.5% SDS, and 50% formamide at 32° C. The term "moderate stringent conditions" refers to conditions of, for example, 5×SSC, 5×Denhardt's solution, 0.5% SDS, and 50% formamide at 42° C. The term "high stringent conditions" refers to conditions of, for example, 5×SSC, 5×Denhardt's solution, 0.5% SDS, and 50% formamide at 50° C. Under these conditions, it can be expected that DNA with higher homology is obtained efficiently at higher temperatures. Multiple factors are involved in hybridization stringency including temperature, probe concentration, probe length, ionic strength, time, salt concentration and others, but persons skilled in the art can appropriately select these factors to achieve similar stringency.

Examples of such a hybridizable polynucleotide include polynucleotides having, e.g., 70% or more, 80% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more identity with the nucleotide sequence of SEQ ID NO: 7, 9 or 11, as calculated by using default parameters under a homology search software, such as FASTA and BLAST. In general, the larger numerical value of the above homology is more preferred.

The identity or homology between amino acid sequences or polynucleotide sequences can be determined using the algorithm BLAST by Karlin and Altschul (Proc. Natl. Acad. Sci. USA, 87: 2264-2268, 1990; Proc. Nail Acad. Sci. U.S.A., 90: 5873, 1993). Programs called BLASTN and BLASTX based on the BLAST algorithm have been developed (Altschul S. F. et al., J. Mol. Biol. 215: 403, 1990). When a nucleotide sequence is analyzed using BLASTN, the parameters are, for example, score=100 and word length=12. When an amino acid sequence is analyzed using BLASTX, the parameters are, for example, score=50 and word length=3. When BLAST and Gapped BLAST programs are used, default parameters for each of the programs are employed.

2. Target Disease in the Present Invention

The invention of the present application provides an rAAV vector useful for treatment of a disease selected from the group consisting of epilepsy, schizophrenia, autism spectrum disorder, mental retardation, anxiety, manic-depressive psychosis, migraine, phobic and compulsive symptoms, drug addiction, Angelman syndrome, dyskinesia, dystonia, Alzheimer's disease, developmental disorders (attention deficit hyperactivity disorder, and Asperger's syndrome), and particularly epilepsy.

Epilepsy refers to pathological conditions in which excessive, synchronous discharging of cerebral nerve cells results in repeated clinical seizures falling in the identical type in one individual (e.g., generalized tonic-clonic seizure, absence seizure, seizure with auditory hallucination, and tonic seizure of a part of extremities). According to the classification of International League Against Epilepsy (ILAE) in 1981, clinical seizures are divided into partial seizures (simple partial seizure and complex partial seizure), generalized seizures (absence seizure, myoclonus seizure, tonic-clonic seizure, atonic seizure), and common variable seizures. Furthermore, according to the "Classification of epilepsy, epilepsy syndrome, and related seizure disorders" of ILAE in 1989, epilepsy is classified into localization-related epilepsy (sub-classified into age-related, symptomatic, cryptogenic epilepsy), generalized epilepsy (sub-classified into idiopathic, cryptogenic or symptomatic epilepsy), cases that cannot be determined to be focal or generalized epilepsy, and special syndrome (e.g., febrile convulsion).

An example of epilepsy with a brief seizure in flexion, which begins at infancy (around 1 year old) as a cardinal sign is West syndrome (or spasmus nutans). This disease forms a series of momentary tonic seizures by which the patient bends his/her upper part of the body and head part forward continuously. There are various causes of West syndrome, and the causes including congenital brain malformation, neurocutaneous syndrome such as tuberous sclerosis, and inborn errors of metabolism such as vitamin B6 deficiency are known. West syndrome is often accompanied by mental retardation, and generally evolves as the patient grows into generalized epilepsy mainly associated with generalized tonic-clonic seizure (grand mal epilepsy), or other types of epilepsy, such as Lennox syndrome, temporal lobe epilepsy, and the like. The rAAV vector of the present invention can have a therapeutic effect against West syndrome.

3. Recombinant Adeno-Associated Virus (rAAV) Vector of the Present Invention

In the invention of the present application, as a vector for delivering a gene to be used for controlling synaptic functions to nervous system cells, a recombinant adeno-associated virus vector (herein also referred to as "vascular-administration-type vector") described in WO 2012/057363, which is capable of efficiently delivering genes to nerve cells also through peripheral administration, or a vector described in WO 2008/124724 etc., can be used, for example. The rAAV vector of the present invention can pass through the blood-brain barrier of a living subject, and thus is capable of introducing a therapeutic gene of interest to nervous system cells of the brain, the spinal cord or the like of a patient by an administration means for delivery to the brain through the blood-brain barrier, such as by peripheral administration to the patient. Moreover, the vector can also be administered intrathecally or directly to a target site in the brain.

The rAAV vector of the present invention can be prepared from preferably natural adeno-associated virus type 1 (AAV1), type 2 (AAV2), type 3 (AAV3), type 4 (AAV4), type 5 (AAV5), type 6 (AAV6), type 7 (AAV7), type 8 (AAV8), type 9 (AAV9) or the like, but examples thereof are not limited thereto. The nucleotide sequences of these adeno-associated viral genomes are known and can be referred to the nucleotide sequences of GenBank accession numbers: AF063497.1 (AAV1), AF043303 (AAV2), NC_001729 (AAV3), NC_001829.1 (AAV4), NC_006152.1 (AAV5), AF028704.1 (AAV6), NC_006260.1 (AAV7), NC_006261.1 (AAV8), and AY530579 (AAV9), respectively. Among them, the types 2, 3, 5 and 9 are human-derived. According to the present invention, it is particularly preferred to use the capsid protein (VP1, VP2, VP3 or the like) derived from AAV1, AAV2 or AAV9. Among human-derived AAVs, AAV1 and AAV9 were reported to have comparatively high multiplicity of infection on nerve cells (Taymans, et al., Hum Gene Ther 18:195-206, 2007, etc.).

A capsid protein to be contained in the rAAV vector used in the present invention is preferably a variant protein, as described in WO2012/057363, WO2008/124724 or the like, which has an amino acid sequence in which at least one tyrosine is substituted with another amino acid such as phenylalanine as compared with the wild-type amino acid sequence. Examples thereof include a variant protein having the amino acid sequence (SEQ ID NO: 9) formed by substitution of tyrosine at position 445 with phenylalanine from the amino acid sequence of a wild-type AAV1 capsid protein, a variant protein having an amino acid sequence (SEQ ID NO: 10) in which the tyrosine residue at position 444 in the amino acid sequence of a wild-type AAV2 capsid protein is substituted with the phenylalanine residue, and a variant protein having the amino acid sequence (SEQ ID NO: 11) in which the tyrosine residue at position 446 in the amino acid sequence of a wild-type AAV9 capsid protein is substituted with the phenylalanine residue (WO2012/057363 and WO 2008/124724). Such a capsid protein has a function of forming a capsomere solely or in combination with the other capsid protein members (for example, VP2 and VP3). Moreover, a polynucleotide comprising a therapeutic gene of interest to be delivered to nervous system cells is packaged in the capsomere.

When the rAAV vector of the present invention is administered into the blood stream, the rAAV vector can pass through the blood-brain barrier of a living subject including an adult and a fetus. In the present invention, examples of nervous system cells as targets of gene transfer include, at least nerve cells contained in the central nervous system such as the brain and the spinal cord, and examples of the cells may further include neuroglial cells, microglial cells, astrocytes, oligodendrocytes, ependymocytes, and cerebrovascular endothelial cells. The percentage of nerve cells in nervous system cells to which a gene is transferred is preferably, 70% or more, 80% or more, 85% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more, or 100%.

The Rep protein used in the present invention may have the same amino acid sequence identity described above, and may contain deletion, substitution, insertion and/or addition of the same number of amino acid residues described above, as long as it has known functions to the same degree such as a function of recognizing an ITR sequence and replicating the genome depending on the sequence, a function of recruiting and packaging a wild-type AAV genome (or rAAV genome) into a viral vector, and a function of forming the rAAV vector of the present invention. Examples of the range of functionally equivalent degrees include ranges described in description concerning the above specific activity. In the present invention, preferably, a Rep protein derived from known AAV3 is used.

A polynucleotide encoding the Rep protein used in the present invention may have the same number of identity described above or may contain deletion, substitution, insertion and/or addition of nucleotides in the same number described above, as long as it encodes a Rep protein having known functions to the same degree, such as a function of recognizing an ITR sequence and replicating the genome depending on the sequence, a function of recruiting and packaging a wild-type AAV genome (or rAAV genome) into a viral vector, and a function of forming the rAAV vector of the present invention. Examples of the range of functionally equivalent degrees include ranges described in description concerning the above specific activity. In the present invention, preferably, a rep protein derived from AAV3 or AAV2 is used.

In an embodiment of the present invention, capsid protein VP1's (VP1, VP2 and/or VP3) encoded by an internal region of the above wild-type AAV genome, and the Rep protein are used through incorporation of a polynucleotide encoding them into an AAV helper plasmid. The capsid proteins (VP1, VP2 and/or VP3) and the Rep protein used in the present invention may be incorporated into one, two, three or more types of plasmid, if necessary. In certain cases, one or more types of these capsid proteins and Rep protein may be contained in the AAV genome. In the present invention, preferably, the capsid proteins (VP1, VP2 and/or VP3) and the Rep protein are all encoded by one type of polynucleotide and provided in the form of an AAV helper plasmid.

A polynucleotide to be packaged in the rAAV vector of the present invention (referred to as the polynucleotide) can be prepared by substituting a polynucleotide of the internal region (specifically, one of or both the rep gene and the cap gene) located between ITR on the 5' side and that on the 3' side of the wild-type genome with a gene cassette containing a polynucleotide encoding a protein of interest (therapeutic gene), a promoter sequence for transcription of the polynucleotide, and the like. Preferably, ITR on the 5' side and that on the 3' side are located at the 5' end and the 3' end of the AAV genome, respectively. Preferably, the rAAV genome of the present invention includes 5'-ITR and 3'-ITR contained in AAV1, AAV2, AAV3, AAV4, AAV8 or AAV9 genome. In general, since an ITR portion easily takes a sequence wherein the complementary sequence is replaced (flip and flop structure), and the 5' to 3' direction may be reversed in the ITR contained in the rAAV genome of the present invention. In the rAAV genome of the present invention, the length of the polynucleotide which is replaced by the internal region (i.e., therapeutic gene) is preferably similar to the length of the original polynucleotide from a practical viewpoint. Specifically, it is preferred that the rAAV genome of the present invention has almost the same size as 5 kb, which is the full length of the wild type genome, for example, about 2 kb to 6 kb, preferably about 4 kb to 6 kb. Except for the length of a transcription regulatory region including a promoter, polyadenylation, etc. (assuming that the length is e.g., about 1 kb to 1.5 kb), the size of a therapeutic gene to be incorporated into the rAAV genome of the present invention preferably ranges from about 0.01 kb to 3.7 kb, more preferably, about 0.01 kb to 2.5 kb, and further preferably, about 0.01 kb to 2 kb, in length, but not limited thereto.

In general, a polynucleotide to be packaged in a recombinant adeno-associated virus vector may take times (several days) until the therapeutic protein of interest is expressed, when the genome is single-stranded. In such a case, a therapeutic gene to be introduced may be designed to be an sc (self-complementary) type in order to exhibit an effect within a shorter time period. Details about this procedure is described in Foust K D, et al. (Nat Biotechnol. 2009 January; 27(1):59-65), for example. The polynucleotide packaged in the rAAV vector of the present invention may be a non-sc type or a sc type.

In an embodiment, the rAAV vector of the present invention comprises a polynucleotide (i.e., such a polynucleotide is packaged) comprising, preferably, a nerve cell-specific promoter sequence and a therapeutic gene operably linked to the promoter sequence. As the promoter sequence to be used in the present invention, a nerve cell-specific promoter sequence is derived from nerve cells, neuroglial cells, oligodendrocytes, cerebrovascular endothelial cells, microglial cells, or ventricular epithelial cells, for example, but the examples thereof are not limited thereto. Specific examples of such promoter sequence include, but are not limited to, a synapsin I promoter sequence, a myelin basic protein promoter sequence, a neuron specific enolase promoter sequence, a glial fibrillary acidic protein promoter sequence, a L7 promoter (cerebellar Purkinje cell specific promoter) sequence, a glutamate receptor delta 2 promoter (cerebellar Purkinje cell specific promoter) sequence, a glial fibrillary acidic protein (hGfa2) promoter sequence, and a glutamic acid decarboxylase (GAD65/GAD67) promoter sequence. Moreover, in the rAAV vector of the present invention, promoter sequences such as a calcium/calmodulin-dependent protein kinase II (CMKII) promoter sequence, a tubulin αI promoter sequence, a platelet-derived growth factor β chain promoter sequence, and the like can also be used. The above promoter sequences may be used independently or in optional combination of two or more thereof. In addition, the above promoter sequences may be strong promoter sequences that are generally used, such as a CMV promoter and a CAG promoter. Examples of particularly preferable promoter sequences in the present invention include a synapsin I promoter sequence, a myelin basic protein promoter sequence, a L7 promoter (cerebellar Purkinje cell specific promoter) sequence, and a glutamate receptor delta 2 promoter (cerebellar Purkinje cell specific promoter). Furthermore, known sequences such as an enhancer sequence which assists in transcription of mRNA, translation into a protein, etc., a Kozak sequence, an appropriate polyadenylation signal sequence, etc may also be contained.

A therapeutic gene of interest to be incorporated into the rAAV genome of the present invention is delivered with high efficiency to nerve cells and then integrated into the genome of the cells. When the rAAV vector of the present invention is used, the therapeutic gene can be transferred to about 10 times more, about 20 times or more, about 30 times or more, about 40 times or more or about 50 times or more of the nerve cell as compared with a conventional rAAV vector. The number of nerve cells carrying the gene transferred thereto can be determined, e.g., by preparing an rAAV vector for packaging the rAAV vector genome with any marker gene incorporated therein, administering the rAAV vector to an animal to be tested, and then measuring the number of nervous system cells expressing the marker gene (or marker protein) incorporated in the rAAV vector genome. The marker gene to be used herein is selected from known genes. Examples of such marker gene include a LacZ gene, a green fluorescence protein (GFP) gene, and a light emitting protein gene (e.g., firefly luciferase).

4. Other Therapeutic Genes

As other means or additional means for improving the excitation-inhibiting function of inhibitory synapses, for example, a means of enhancing the expression of neurexin 1α that is a binding partner of neuroligin 2, and a means of improving the intracellular signal transduction of neuroligin 2 can be expected. Alternatively, as such other means or additional means, a means of lowering the functions of excitatory synapses, such as suppressing the expression of a protein involving the operation of excitatory synapses, which is specifically a means of reducing the number of neuroligin 1 by using the antisense of neuroligin 1 (Non Patent Literature 4: Fang et al., Mol. Neurobiol. 2014 November) can also be useful.

The rAAV vector of the present invention may express different proteins for controlling synaptic functions. Examples of such different proteins include neutralizing antibodies against proteins and receptors existing on synaptic membranes (including antigen-binding sites, Fab, Fab2, single-chain antibody (scFv), etc.). Examples of the classes of these antibodies include IgG, IgM, IgA, IgD, and IgE.

For example, for inhibition of the functions of excitatory synapses, a therapeutic gene to be incorporated into the rAAV genome of the present invention may be a polynucleotide for modifying (for example, disrupting or lowering) a function of a target endogenous gene, or a polynucleotide for changing (for example, lowering) an expression level of an endogenous protein, such as an antisense molecule, a ribozyme, interfering RNA (iRNA), and micro RNA (miRNA). For example, in order to effectively inhibit the expression of a target gene by using an antisense sequence, preferably, the length of an antisense nucleic acid is 10 or more nucleotides, 15 or more nucleotides, 20 or more nucleotides, or 100 or more nucleotides, or even more preferably 500 or more nucleotides. In general, the length of an antisense nucleic acid to be used is shorter than 5 kb, and is preferably shorter than 2.5 kb.

By using a ribozyme, the mRNA encoding a protein of interest can be specifically cleaved to decrease the expression of the protein. For the design of such a ribozyme, reference may be made to various known publications (see e.g., FEBS Lett. 228: 228, 1988; FEBS Lett. 239: 285, 1988; Nucl. Acids. Res. 17: 7059, 1989; Nature 323: 349, 1986, etc.).

The term "RNAi" refers to a phenomenon that, when a double-stranded RNA with a sequence identical or similar to a target gene sequence is introduced into cells, expression of both a target foreign gene introduced and the target endogenous gene is decreased. Examples of RNA used herein include double-stranded RNA of 21 to 25 nucleotides in length that triggers RNA interference, such as dsRNA (double strand RNA), siRNA (small interfering RNA), shRNA (short hairpin RNA) or miRNA (microRNA). These RNAs can be locally delivered to a desired site by a delivery system using liposomes, or a vector that generates the double-stranded RNA described above can be used for local expression thereof. Methods for preparing or using such double-stranded RNA (dsRNA, siRNA, shRNA or miRNA) are known from many publications (see, e.g., National Publication of International Patent Application No. 2002-516062, U.S. Pat. No. 2002/086356A, Nature Genetics, 24(2), 180-183, 2000 February).

To use these other therapeutic genes, for example, a known internal ribosome entry site (IRES) sequence is allowed to intervene in a polynucleotide contained in the vector of the present invention. When the rAAV genome of the present invention is a non-sc type, it is possible to select promoters with more varied lengths and genes of interest, and also a plurality of genes of interest. A polynucleotide to be packaged in the rAAV vector of the present invention has a full length of preferably about 5 kb or less (about 4.7 kb or less when an ITR region is excluded).

5. Preparation of the rAAV Vector of the Present Invention

A general method can be employed as a method for preparing the rAAV vector of the present invention. For example, the method may comprise a step of transfecting a cultured cell with: (a) a first polynucleotide encoding a capsid protein (generally referred to as an AAV helper plasmid), and (b) a second polynucleotide (carrying a therapeutic gene of interest) to be packaged in the rAAV vector of the present invention; and may further comprise a step of transfecting the cultured cell with (c) a plasmid encoding an adenovirus-derived factor, also referred to as an adenovirus (AdV) helper plasmid, or a step of infecting cultured cells with an adenovirus. The method can also comprise a step of culturing the transfected cultured cell and a step of collecting the recombinant adeno-associated virus vector from the culture supernatant. Furthermore, (d) an example of a method for preparing the rAAV vector of the present invention includes a method for producing an rAAV in a large scale by preparing baculoviruses containing the above polynucleotides (a) and (b), respectively, and then infecting insect cells, Sf9 or the like with the viruses. This method is already known and also used in Examples of the Description.

A nucleotide encoding the capsid protein of the present invention in the first polynucleotide (a) is preferably operably bound to a known promoter sequence that is operable in cultured cells. As such a promoter sequence, for example, a cytomegalovirus (CMV) promoter, an EF-1α promoter, an SV40 promoter, and the like can be appropriately used. Furthermore, the first polynucleotide can comprise a known enhancer sequence, a Kozak sequence, a polyA addition signal sequence and the like, as appropriate.

The second polynucleotide (b) comprises a therapeutic gene at a position where it is operable with a nervous system cell-specific promoter. Furthermore, the second polynucleotide can comprise a known enhancer sequence, a Kozak sequence, a polyA addition signal sequence, and the like as appropriate. The first polynucleotide can further comprise a cloning site, which can be cleaved by various known restriction enzymes, and is located downstream from the nervous system cell-specific promoter sequence. A multicloning site containing a plurality of restriction enzyme recognition sites is more preferred. Persons skilled in the art may incorporate a therapeutic gene of interest downstream of the nervous system cell-specific promoter, in accordance with known genetic engineering procedures. For such genetic engineering procedures, see, e.g., Molecular Cloning 3rd Edition, J. Sambrook et al., Cold Spring Harbor Lab: Press. 2001, etc.

In preparation of the rAAV vector of the present invention, a helper virus plasmid (e.g., adenovirus, herpes virus or vaccinia) is used and can be introduced into cultured cells simultaneously with the above first and second polynucleotides. Preferably, the preparation method of the present invention further comprises a step of introducing an adenovirus (AdV) helper plasmid. In the present invention, preferably, AdV helper is derived from a virus of the same species as that of cultured cells. For example, when human cultured cells 293T are used, a human AdV-derived helper virus vector can be used. As such an AdV helper vector, a commercially available AAV Helper-Free System (Agilent Technologies, catalog No. 240071) can be used, for example.

In preparation of the rAAV vector of the present invention, examples of a method for transfecting cultured cells with the above one or more types of plasmid, which can be used herein, include various known methods such as the calcium phosphate method, lipofection method, and electroporation method, etc. Such methods are described in, e.g., Molecular Cloning 3rd Ed., Current Protocols in Molecular Biology, John Wiley & Sons 1987-1997, etc.

6. Pharmaceutical Composition Containing the rAAV Vector of the Present Invention The rAAV vector of the present invention can comprise genes useful for treatment of neurological disorders, particularly, diseases relating to protein dysfunction in synapses (e.g., schizophrenia and autism spectrum disorder). The rAAV vector comprising these genes can be administered intravascularly to pass through the blood-brain barrier, and thus can be incorporated into nerve cells of the brain, the spinal cord, and the retina. The rAAV vector comprising such a therapeutic gene can be contained in the pharmaceutical composition of the present invention. As such therapeutic genes, for example, polynucleotides encoding the above-mentioned antibodies, neurotrophic factor (NGF), growth factor (HGF), acidic fibroblast growth factor (aFGF), miRNA and the like can be selected. It can be expected to treat neurological disorder through peripheral administration of such rAAV vector to a test subject.

The active ingredient of the pharmaceutical composition of the present invention may be formulated solely or in combination therein, and can also be provided as a pharmaceutical preparation by formulation with a pharmaceutically acceptable carrier or an additive for a pharmaceutical preparation. In this case, the active ingredient of the present invention may be contained in an amount e.g., 0.1 to 99.9 wt % in the preparation.

Examples of the pharmaceutically acceptable carriers or additives that can be used include excipients, disintegrants, disintegration aids, binders, lubricants, coating agents, dyes, diluents, dissolution agents, dissolution aids, isotonic agents, pH regulators, stabilizers, etc. For oral administration, excipients that are generally used in the art, such as microcrystalline cellulose, sodium citrate, calcium carbonate, disintegrants such as starch and alginic acid, granulation binders such as polyvinylpyrrolidone, and lubricants can be used in combination. When aqueous suspensions and/or elixirs are desired for oral administration, the active ingredient may be used in combination with various sweeteners or corrigents, coloring agents or dyes, and, if necessary, emulsifying and/or suspending agents as well, together with diluents such as water, ethanol, propylene glycol, glycerin, etc. and combinations thereof.

Examples of the pharmaceutical preparations suitable for oral administration can include powders, tablets, capsules, fine granules, granules, liquids or syrups, etc. Examples of the pharmaceutical preparations suitable for parenteral administration can include injections, intrathecal injections, suppositories, etc. For parenteral administration, solutions of the active ingredient of the present invention dissolved in either sesame or peanut oil or in aqueous propylene glycol solution may be employed. The aqueous solutions should be appropriately buffered (preferably pH 8 or higher) as necessary; it is first necessary to render the liquid diluent isotonic. As such a liquid diluent, physiological saline can be used. The thus prepared aqueous solutions are suitable for intravenous injection. On the other hand, the oily solutions are suitable for intra-articular injection, intra-muscular injection and subcutaneous injection. The preparation of all these solutions under sterile conditions can be readily accomplished by standard pharmaceutical techniques well known to those skilled in the art. Furthermore, the active ingredient of the present invention can also be administered topically to the skin, etc. In this case, topical administration is desirably performed by way of creams, jellies, pastes, ointments and the like, in accordance with standard pharmaceutical practice.

The dose of the pharmaceutical composition of the present invention is not particularly limited, and an appropriate dose can be chosen depending on various conditions such as type of disease, age and symptoms of the patient, administration route, therapeutic goal, presence or absence of concurrent drugs, etc. The dose of the pharmaceutical composition of the present invention is, but not limited to, for example, 1 to 5,000 mg, and preferably 10 to 1,000 mg per day for an adult (e.g., body weight of 60 kg). Such daily dose may be administered in 2 to 4 divided doses per day. When vg (vector genome) is used as a dosage unit, the dose can be selected from, but not limited to, e.g., the range from $10^9$ to $10^{14}$ vg, preferably, $10^{10}$ to $10^{13}$ vg, and more preferably, $10^{10}$ to $10^{12}$ vg per kg body weight.

7. Administration of the rAAV Vector of the Present Invention

The rAAV of the present invention is capable of passing through the blood-brain barrier of a living subject (including incomplete fetal and newborn blood-brain barriers, and established adult blood-brain barriers) and thus capable of delivering genes in the rAAV to nervous system cells of the brain, the spinal cord, and the like through peripheral administration to a living subject (including adults and fetuses or newborns). Furthermore, the rAAV vector to be used in the present invention can target nerve cells contained in an adult's brain, spinal cord, and the like through peripheral administration. As used herein, the term "peripheral administration" refers to administration routes which those skilled in the art usually understand as peripheral administration, including intravenous administration, intraarterial administration, intraperitoneal administration, intracardiac administration, intramuscular administration, and umbilical intravascular administration (e.g., the target is a fetus), and so on. Furthermore, an administration method, which involves using a fluid other than blood that is fluidly communicated with the brain, such as intrathecal administration, can also be used for the rAAV vector of the present invention. In another embodiment, the rAAV vector of the present invention can also be locally administered to a target site within the brain, such as hippocampi. For example, when the rAAV of the present invention is administered via intrathecal administration into a spinal fluid, or via peripheral administration into blood, a means for administration simpler than intraparenchymal administration can be provided.

8. Kit for Preparation of the rAAV Vector of the Present Invention

In another embodiment, the present invention provides a kit for preparing the rAAV of the present invention. Such a kit can contain, for example, (a) a first polynucleotide for expression of capsid protein VP1 or the like, and (b) a second polynucleotide to be packaged in the rAAV vector. For example, the first polynucleotide comprises a polynucleotide encoding the amino acids of SEQ ID NO. For example, the second polynucleotide may or may not comprise a therapeutic gene of interest, but can preferably comprise various restriction enzyme cleavage sites for incorporation of such a therapeutic gene of interest.

The kit for preparing the rAAV vector of the present invention can further contain any component described herein (e.g., an AdV helper). The kit of the present invention may further include instructions describing the protocols for preparation of the rAAV vector using the kit of the present invention.

9. Chemotherapeutic Agent to be Used in Combination with the rAAV of the Present Invention The rAAV vector according to the invention of the present application can also be used in combination with an existing chemotherapeutic agent. Examples of such a chemotherapeutic agent include phenytoin, carbamazepine, valproic acid, topiramate, lamotrigine, rufinamide, phenobarbital, diazepam, clonazepam, ethosuximide, zonisamide, gabapentin, levetiracetam, midazolam, clobazam, and propofol. For example, after administration of the rAAV of the invention of the present application, a significant reduction in the dose of the above chemotherapeutic agent can be expected.

10. Determination of Therapeutic Effects

The therapeutic effects of the rAAV vector of the present invention can be determined using a known means for determining if excitation can be inhibited by the therapeutic effects. Examples of such a known means include, but are not limited to, analysis of behavior levels, analysis of the pharmacodynamics of labeled transmitters (e.g., GABA), measurement of excitatory postsynaptic potential and inhibitory postsynaptic potential, measurement of changes in threshold of epilepsy induced by medicines or electric stimulation, brain wave, optical topography, and positron emission tomography (PET).

11. Terms Used in the Description

The meaning indicated by each term as used herein is as described below. Terms not particularly described herein are intended to refer to meanings that are normally understood by persons skilled in the art.

As used herein, the terms "virus or viral vector", "virus virion," and "virus or viral particles" are interchangeably used, unless otherwise indicated.

As used herein, the term "nervous system" refers to an organ system made up of nerve tissues. As used herein, the term "nervous system cells" include at least nerve cells included in the central nervous system including brains, spinal cords, etc. and may further include neuroglial cells, microglial cells, astrocytes, oligodendrocytes, ependymocytes, cerebrovascular endothelial cells, etc.

As used herein, the term "polynucleotide" is interchangeably used with "nucleic acid," "gene" or "nucleic acid molecule," which is intended to mean a nucleotide polymer. As used herein, the term "nucleotide sequence" is used interchangeably with "nucleic acid sequence" or "base sequence," which is represented by a sequence of deoxyribonucleotides (abbreviated as A, G, C, and T). For example, the "polynucleotide comprising the nucleotide sequence of SEQ ID NO: 1 or a fragment thereof" is intended to mean a polynucleotide comprising a sequence shown by the respective deoxynucleotides A, G, C and/or T of SEQ ID NO: 1, or a fragment thereof.

Each of "virus or viral genome" and "polynucleotide" according to the present invention may exist in the form of a DNA (e.g., cDNA or genomic DNA), respectively, and may also be in the form of an RNA (e.g., mRNA). Each of the viral genome and the polynucleotide as used herein may be a double-stranded or single-stranded DNA. Single-stranded DNA or RNA may be a coding strand (also known as a sense strand) or a non-coding strand (also known as an anti-sense strand). Regarding the explanation herein for placing a promoter, a gene of interest, polyadenylation signal, etc. in the gene, which are encoded by the rAAV genome, if the rAAV genome is a sense strand, the strand itself is described and if it is an antisense strand, its complementary strand is described, unless otherwise specified.

As used herein, the terms "protein" and "polypeptide" are interchangeably used and intended to mean a polymer of amino acids. The polypeptide as used herein is represented in accordance with conventional peptide designation, in which, the N-terminus (amino terminus) is on the left hand and the C-terminus (carboxyl terminus) on the right hand. The partial peptide in the polypeptide of the present invention (as used herein, may briefly be referred to as the partial peptide of the present invention) includes a partial peptide of the polypeptide of the present invention described above, preferably having the same properties as those of the above polypeptide of the present invention.

As used herein, the term "plasmid" refers to various known gene elements, for example, a plasmid, a phage, a transposon, a cosmid, a chromosome, etc. The plasmid can be replicated in a particular host and transport gene sequences between cells. As used herein, the plasmid contains various known nucleotides (DNA, RNA, PNA and a mixture thereof) and may be a single strand or a double strand, and preferably a double strand. As used herein, the term "rAAV vector plasmid" is intended to include a double strand formed by rAAV vector genome and its complementary strand, unless otherwise specified. The plasmid used in the present invention may be linear or circular.

As use herein, the term "packaging" refers to the events including preparation of single-stranded viral genomes, assembly of coat (capsid) proteins, enclosure of viral genome within a capsid (encapsidation), and the like. When an appropriate plasmid vector (normally, a plurality of plasmids) is introduced into a cell line that allows packaging under appropriate conditions, recombinant viral particles (i.e., virus virions, viral vectors) are constructed and secreted into the culture.

EXAMPLES

The present invention is described below in more detail by referring to Examples, but the scope of the invention should not be limited to the following Examples.

Experimental Outline

Intracardiac administration of rAAV-Neuroligin2 (rAAV-NL2) at 6 weeks of age

For: —Seizure frequency—Duration—Intensity—Duration×Intensity—Changes in threshold for electric stimulation Intracerebral expression of neuroligin2-carrying intravascular-administration-type rAAV Reports concerning the gene therapy for epilepsy using model animals are found here and there, but they all involve performing topical administration stereotactically. For application to a human patient, administration methods without invasive procedures are desired. This time, the inventors of the present application prepared an intravascular-administration-type adeno-associated virus (rAAV) vector, administered the vector to EL mice naturally developing epilepsy (Suzuki, Proc. Jpn. Acad., Ser.B89 (2013)), and then observed the condition of intracerebral expression and the presence or the absence of an effect of suppressing seizure.

Experimental Materials and Methods

Recombinant Adeno-Associated Virus (rAAV) Vector

The vector to be used in the Examples is previously disclosed AAV9/3 (having tyrosine mutation (Y446→F) introduced into AAV9 capsid, and ITR of AAV3) carrying a Synapsin I promoter (WO 2012/057363). To differentiate from endogenous Neuroligin 2 (NL2), an rAAV vector expressing neuroligin2 with the N-terminus, to which a FLAG tag (DDDDK) sequence had been bound, was prepared (AAV9/3-Syn1-FLAG (DDDDK)-NL2), and then administered to subject animals.

Administration to Animal

EL mice (6 weeks of age, male, body weight: 22-32 g) were used.

Under 2-4% sevoflurane anesthesia, inracardiac injection of AAV9/3-Syn1-FLAG (DDDDK)-NL2 was performed at $4.1\times10^{13}$ vector genome/ml×0.1 ml/mouse (NL2 intracardiac injection group n=10). A group to which AAV9/3-Syn1-AcGFP-WPRE was administered via intracardiac injection at $2.3\times10^{13}$ vg/ml×0.1 ml/mouse (n=17), and a group to which only physiological saline was administered at 0.1 ml/mouse (n=14) were designated as control groups. Also, for comparison with topical administration, a group of mice to which AAV9/3-Syn1-FLAG (DDDDK)-NL 2 was injected to the bilateral hippocampal CA3 region (0.5 mm anterior to and 3.0 mm lateral to bregma, and 2.0 mm from the brain surface) at $4.1\times10^{13}$ vg/ml×0.005 ml (n=3) was designated as the topical administration group.

TABLE 1

| | Administration site | Titer vg/mouse | Number of mice |
|---|---|---|---|
| rAAV-NL2 | Intracardiac | $4.1 \times 10^{12}$ | 10 |
| rAAV-GFP | Intracardiac | $2.3 \times 10^{12}$ | 17 |
| Physiological saline | Intracardiac | — | 14 |
| rAAV-NL2 | Bilateral hippocampi | $2.0 \times 10^{11}$ | 3 |
| rAAV-GFP | Bilateral hippocampi | $1.1 \times 10^{11}$ | 3 |
| Physiological saline | Bilateral hippocampi | — | 3 |

Evaluation by Angular Acceleratory Stimulation

After administration of the vector and the like, each of the mice was rotated with the tail held for predetermined times (8 rotations) every week until 22 weeks of age, and the behavior of each of the mice was video-recorded. Thereafter, the presence or the absence of seizures, duration when a mouse had developed a seizure, and the intensity thereof were observed on video.

Seizure intensity was scored as follows:
1 point: no seizure;
2 points: only raised the tail or only shook the body;
3 points: developed a clear seizure, but kept the posture without falling down; and
4 points: developed a severe seizure and could not keep the posture and fell down sideways.

Seizure duration was scored as follows:
1 point: no seizure;
2 points: 1-10 seconds;
3 points: 11-20 seconds;
4 points: 21-30 seconds;
5 points: 31-60 seconds; and
6 points: 61 seconds or longer.

The seizure incidence, the mean seizure duration, the mean seizure intensity, and the mean seizure duration× intensity of each group were evaluated every week.

Evaluation by Electric Stimulation

At 5 (before administration of the vector), 12, 18, 22 weeks of age, electrodes were placed on both ears of a mouse, electric stimulation (the following parameters were used in Neuropack S1 (NIHON KOHDEN): duration: 1 ms, interval: 50 ms, 10 train, strength: max 50 mA every 0 mA to 5 mA) was applied to induce an epileptic seizure, and then the seizure threshold was measured. If no seizure was induced by 50 mA, the seizure threshold was determined to be 60 mA for evaluation. For only the topical administration group of mice, this procedure was performed at 5, 12, and 22 weeks of age.

Statistical Processing was Evaluated by the Following Tests.
Seizure incidence: Fisher's exact test
Other: Welch's t test Histological Analysis Preparation of brain specimen: Each mouse was deeply anesthetized with pentobarbial, and then 4% paraformaldehyde-containing 0.1M phosphate buffer (pH7.4) was injected through the left ventricle for perfusion fixation. After fixation, the brain was dissected out, immersion fixed in a fixative for a half day, transferred into 15% sucrose-containing 0.1M phosphate buffer (pH 7.4), and then stored in a refrigerator until a histochemical experiment.

rAAV9-GFP Expression and Cell Identification

40-µm sagittal sections were prepared using a cryomicrotome and then GFP expression was identified at each brain site using a fluorescence microscope. GFP-expressing cells were identified by double staining with the following markers.

Nerve cells: NeuN or MAP2; glial cells: GFAP; and inhibitory interneurons: Parvalbumin rAAV9-NL2 Expression and Cell Identification In a manner similar to that in identification of GFP, 40-µm sagittal sections were prepared, and the transgene NL2 expression was identified by FLAG (DDDDK) antibody staining. FLAG antibody was purchased from Abcam plc., and the expression was identified under a fluorescence microscope by image processing using a Alexafluor 488 conjugated secondary antibody.

Experimental Results and Discussion

Hippocampal slices (specimens) were subjected to measurement of changes in intracellular $Ca^{2+}$ influx upon ischaemic loading based on changes in fluorescence of rhod 2-AM (DOJINDO catalog No.: R002). As compared with DDY mice, EL mice exhibited, in the CA3 region, significant increases in intracellular $Ca^{2+}$ influx induced in hippocampi by ischaemiac loading, suggesting the vulnerability of the inhibitory system in the CA3 region. Next, the expression of intervening cells of an excitation inhibition system in EL hippocampi was histologically examined by immunostaining with the parvalbumin antibody (catalog No.: LS-C39101). No significant difference was found between EL mice and DDY mice in terms of the number of parvalbumin-positive cells in each hippocampal region, suggesting possible changes at the synaptic level. Based on the above results, an rAAV vector expressing a gene of an inhibitory system synapse-related molecule was prepared, the vector was administered to EL via stereotactic hippocampal injection and intravascular injection, and then intracerebral distribution was histologically observed by staining using a FLAG antibody (FIG. 1a, and FIG. 1b). As shown in FIG. 1a, FLAG-tagged NLGN2 was broadly expressed in hippocampal and cerebral cortical nerve cells as a result of intravascular administration of the vector the present invention, so that successful gene delivery by rAAV could be confirmed.

Subsequently, the intravascular injection group was observed for the presence or the absence of the effect of suppressing epileptic seizure (FIG. 2 to FIG. 6). A group to which a green fluorescent protein EGFP expression AAV vector was administered, and a group to which physiological saline was administered were designated as control groups. The effect of suppressing epilepsy was evaluated for each attribute; that is, frequency of seizure development, intensity, duration, and seizure intensity×duration of a mouse at each age in weeks. In addition, significant differences were observed at positions marked with "*" and "**" in the figures. The group to which NLGN2 had been administered suppressed seizures more significantly than the control groups, and exhibited no change in threshold for electric stimulation (FIG. 2 to FIG. 6). No change in threshold for electric stimulation suggested that the initiation of the operation of inhibitory synapses remained unchanged from the time before introduction and suggested the low side effect.

Expression of the gene of interest was observed in hippocampal neurons of the hippocampal injection group, and in whole brain neurons including hippocampal neurons of the intravascular administration group (the results not shown). Compared with the control groups, the hippocampal injection group, specifically, the group to which NLGN2 had been administered exhibited a significant difference in seizure frequency in some cases, but exhibited overall no significant difference in the effect (FIG. 7 to FIG. 11). In the figures, significant differences were observed for those indicated with "*" and "**". Moreover, compared with the intracardiac administration groups, the intracardiac administration groups were generally observed to tend to exhibit the higher effects on suppressing epilepsy than the other groups in any attribute of seizure frequency, seizure duration and seizure intensity.

The target molecules were supplied to whole brain neurons by the intravascular-administration-type AAV vector. The excitation inhibitory effect of said molecules is capable of suppressing epileptic seizures without changing the threshold for electric stimulation, suggesting a possibility of a non-invasive epilepsy gene therapy as a more advantageous therapeutic method.

INDUSTRIAL APPLICABILITY

The use of the rAAV vector of the present invention can be expected to treat (e.g., alleviation, improvement, and repair) genetic malfunctions in nervous system cells (including congenital and acquired malfunctions).

Sequence Listing Free Text

SEQ ID NO: 1: human neuroligin2 nucleotide sequence
SEQ ID NO: 2: human neuroligin2 amino acid sequence
SEQ ID NO: 3: mouse neuroligin2 nucleotide sequence
SEQ ID NO: 4: mouse neuroligin2 amino acid sequence
SEQ ID NO: 5: rat neuroligin2 nucleotide sequence
SEQ ID NO: 6: rat neuroligin2 amino acid sequence
SEQ ID NO: 7: Flag-tagged mouse neuroligin2 nucleotide sequence
SEQ ID NO: 8: Flag-tagged mouse neuroligin2 amino acid sequence
SEQ ID NO: 9: AAV1 capsid protein Y445F variant amino acid sequence
SEQ ID NO: 10: AAV2 capsid protein Y444F variant amino acid sequence
SEQ ID NO: 11: AAV9 capsid protein Y446F variant amino acid sequence

The invention claimed is:

1. A method for reduction in intensity, duration or frequency of seizures due to epilepsy in a subject, which comprises administrating by intracranial or intracardiac administration to the subject a pharmaceutical composition comprising a recombinant adeno-associated virus vector, wherein the vector comprises:
   a polynucleotide comprising a nucleotide sequence encoding a neuroligin 2 protein which comprises the amino acid sequence of SEQ ID NO: 2, 4 or 6, and
   a capsid protein having a variant amino acid sequence which has the amino acid sequence of SEQ ID NO:11, and optionally one or more tyrosine residues in the sequence substituted with phenylalanine.

2. The method according to claim 1, which is used in combination with a chemotherapeutic agent for a neuropsychiatric disease.

3. The method according to claim 1, wherein the polynucleotide comprises a promoter sequence selected from the group consisting of a synapsin I promoter sequence, a myelin basic protein promoter sequence, a neuron specific enolase promoter sequence, a calcium/calmodulin-dependent protein kinase II (CMKII) promoter sequence, a tubulin «1 promoter sequence, a platelet-derived growth factor β chain promoter sequence, a glial fibrillary acidic protein (GFAP) promoter sequence, a L7 promoter sequence, a glial fibrillary acidic protein 2 (Gfa2) promoter sequence, a glutamate receptor delta 2 promoter sequence, a glutamic acid decarboxylase (GAD) 65 promoter sequence, and a GAD67 promoter sequence.

4. The method according to claim 1, wherein the polynucleotide comprises an inverted terminal repeat (ITR) selected from the group consisting of AAV1, AAV2, AAV3, AAV4, AAV8, and AAV9.

5. The method according to claim 1, wherein the polynucleotide further comprises a polynucleotide for inhibiting the excitation of excitatory synapses.

6. The method according to claim 1, which is administered by topical hippocampal administration.

* * * * *